US011053483B2

(12) United States Patent
Gjermansen et al.

(10) Patent No.: US 11,053,483 B2
(45) Date of Patent: Jul. 6, 2021

(54) POLYPEPTIDES HAVING DNASE ACTIVITY

(71) Applicant: Novozymes A/S, Bagsvaerd (DK)

(72) Inventors: Morten Gjermansen, Greve (DK); Jesper Salomon, Holte (DK); Klaus Gori, Dyssegaard (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 16/495,158

(22) PCT Filed: Mar. 23, 2018

(86) PCT No.: PCT/EP2018/057469
§ 371 (c)(1),
(2) Date: Sep. 18, 2019

(87) PCT Pub. No.: WO2018/177936
PCT Pub. Date: Oct. 4, 2018

(65) Prior Publication Data
US 2020/0024584 A1 Jan. 23, 2020

(30) Foreign Application Priority Data
Mar. 31, 2017 (EP) .................................... 17164351
Jul. 7, 2017 (EP) .................................... 17180195

(51) Int. Cl.
C12N 9/22 (2006.01)
C12N 1/14 (2006.01)
C12N 1/20 (2006.01)
C11D 3/386 (2006.01)
C12N 15/75 (2006.01)

(52) U.S. Cl.
CPC ............ C12N 9/22 (2013.01); C11D 3/38636 (2013.01); C12N 1/14 (2013.01); C12N 1/20 (2013.01); C12N 15/75 (2013.01)

(58) Field of Classification Search
None
See application file for complete search history.

(56) References Cited

U.S. PATENT DOCUMENTS

2002/0081622 A1* 6/2002 Adams .................... C07K 16/40
435/7.1
2010/0075376 A1* 3/2010 Rasmussen .............. C12N 1/08
435/69.1

(Continued)

FOREIGN PATENT DOCUMENTS

EP 2617824 A1 7/2013
EP 3088505 A1 11/2016
WO 2015/166075 A1 11/2015

OTHER PUBLICATIONS

UniProt Accession No. A0A1D7VWD2_9ACTN, published Jan. 18, 2017 (Year: 2017).*

(Continued)

Primary Examiner — Richard C Ekstrom
(74) Attorney, Agent, or Firm — Elias Lambiris

(57) ABSTRACT

The present invention relates to polypeptides having DNase activity and polynucleotides encoding the polypeptides. The invention also relates to nucleic acid constructs, vectors, and host cells comprising the polynucleotides as well as methods of producing and using the polypeptides.

19 Claims, 1 Drawing Sheet
Specification includes a Sequence Listing.

(56) References Cited

U.S. PATENT DOCUMENTS

2016/0319225 A1* 11/2016 Lant .................. C11D 3/38627
2020/0024584 A1* 1/2020 Gjermansen ........... C12N 15/75

OTHER PUBLICATIONS

Gen Bank Accession No. WP_069573498.1, published Oct. 27, 2016 (Year: 2016).*
Gen Bank Accession No. WP_033428329.1, published Oct. 26, 2016 (Year: 2016).*
Gen Bank Accession No. WP_025361737.1, published Oct. 27, 2016 (Year: 2016).*
Jia et al, 2017, EBI Accession No. A0A1D7VWD2.
Mori et al, 2014, EBI Accession No. JC204385.
Mori et al, 2014, EBI Accession No. JC204387.

* cited by examiner

| | | | |
|---|---|---|---|
| SEQ ID NO 9 Kutzneria albida | TPPNIPDKTAVNELNGIRVQPDGSSAGYSRDKFKHWLIIEGSCNTREMV |
| SEQ ID NO 3 Saccharothrix australiensis | TPPDIPGTATAQAELAGLTVAAEGSTAGYSRDLFPHWTIVSGTCNTREIV |
| SEQ ID NO 6 Streptomyces sp-63712 | APPSPPSAATARTYLTEIKEQPEGPQDGYSRDKFPHWIDQGNNCNTREVV |

| | |
|---|---|
| SEQ ID NO 9 Kutzneria albida | LKRDGTNVQTDSSCAAKSGTWYSPYDGSTQTSASAIQIDHMVPLADAWRT |
| SEQ ID NO 3 Saccharothrix australiensis | LKRDGTSVVTDASCAATSGRWYSPYDGATWSAASDVDIDHVVPLAFAWRS |
| SEQ ID NO 6 Streptomyces sp-63712 | LKRDGTNVQQDGSCAAVGGTWVSAYDGATWTQASDLDIDHVVPLSEAWKS |

| | |
|---|---|
| SEQ ID NO 9 Kutzneria albida | GASGWTAQRRQDFANDLSYPQLVAVKGAVNESKGDKSPDLMKPPLTSYWC |
| SEQ ID NO 3 Saccharothrix australiensis | GASSWTIARRQSFANDIAGPQLIAVTDDVNQAKGDQDPARWQPPLTSYRC |
| SEQ ID NO 6 Streptomyces sp-63712 | GAAQWTIAKRQELANDITHSQLIAVTDNVNQAKGDKDPANMLPPKASYHC |

| | |
|---|---|
| SEQ ID NO 9 Kutzneria albida | TYAKMWTHVKSKYSLTVNSAEKSALQDMLGRC |
| SEQ ID NO 3 Saccharothrix australiensis | LYAKMWVHTKHRWGLKVDSAEKSALQSMLGRC |
| SEQ ID NO 6 Streptomyces sp-63712 | EYARMLWWVKHEYGMTADSAEKAALKKILDGC |

POLYPEPTIDES HAVING DNASE ACTIVITY

CROSS-REFERENCE TO RELATED APPLICATIONS

This application is a 35 U.S.C. 371 national application of international application no. PCT/EP2018/057469 filed Mar. 23, 2018, which claims priority or the benefit under 35 U.S.C. 119 of European application nos. EP 17164351.3 filed Mar. 31, 2017 and EP 17180195.4 filed and Jul. 7, 2017, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides having DNase activity and polynucleotides encoding the polypeptides. The invention also relates to nucleic acid constructs, vectors, and host cells comprising the polynucleotides as well as methods of producing and using the polypeptides.

Description of the Related Art

Enzymes have been used in detergents for decades. Usually a cocktail of various enzymes is added to detergent compositions. The enzyme cocktail often comprises various enzymes, wherein each enzyme targets it specific substrate e.g. amylases are active towards starch stains, proteases on protein stains and so forth. Textiles and surfaces such as laundry and dishes becomes soiled with many different types of soiling. The soiling may be composed of proteins, grease, starch etc. One type of soiling comes from organic matter such as biofilm. The presence of biofilm provides several disadvantages. Biofilm comprises an extracellular polymeric matrix, composed of polysaccharides, extracellular DNA (eDNA), and proteins. The extracellular polymeric matrix may be sticky or gluing, which when present on textile, gives rise to redeposition or backstaining of soil resulting in a greying of the textile. Another drawback is that malodor may be trapped within the organic structure. Organic matter such as biofilm is therefore not desirable in textiles and surfaces associated with cleaning such as washing machines etc. As organic soiling is a complex mixture of polysaccharides, proteins, DNA etc. there is a need for enzymes which effectively prevent, remove or reduce components of such soiling e.g. DNA on items such of fabrics.

SUMMARY OF THE INVENTION

The present invention relates to polypeptides having DNase activity. In particular the invention relates to polypeptides selected from the group consisting of:
(a) a polypeptide having at least 80% sequence identity to the polypeptide of SEQ ID NO: 3;
(b) a polypeptide having at least 80% sequence identity to the polypeptide of SEQ ID NO: 6;
(c) a polypeptide having at least 80% sequence identity to the polypeptide of SEQ ID NO: 9;
(d) a variant of the polypeptide selected from the group consisting of SEQ ID NO: 3, SEQ ID NO: 6 and SEQ ID NO: 9, wherein the variant has DNase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions;
(e) a polypeptide comprising the polypeptide of (a) to (d) and a N-terminal and/or C-terminal His-tag and/or HQ-tag;
(f) a polypeptide comprising the polypeptide of (a) to (d) and a N-terminal and/or C-terminal extension of between 1 and 10 amino acids; and
(g) a fragment of the polypeptide of (a) to (d) having DNase activity and having at least 90% of the length of the mature polypeptide.

The invention further relates to a composition e.g. a cleaning or detergent composition, an automatic dish wash (ADW) composition or a laundry composition, comprising a polypeptide according to the invention.

The invention further relates to use of a polypeptide according to the invention for deep cleaning of an item, such as textile e.g. fabric. The invention further relates to the use of a DNase according to the invention,
(i) for preventing, reducing or removing stickiness of the item;
(ii) for pretreating stains on the item;
(iii) for preventing, reducing or removing redeposition of soil during a wash cycle;
(iv) for preventing, reducing or removing adherence of soil to the item;
(v) for maintaining or improving whiteness of the item;
(vi) for preventing, reducing or removal malodor from the item,
wherein the item is a textile.

The invention also relates to a method for laundering an item comprising the steps of:
a. Exposing an item to a wash liquor comprising a polypeptide according to the invention or a cleaning composition comprising a polypeptide according to the invention;
b. Completing at least one wash cycle; and
c. Optionally rinsing the item,
wherein the item is a textile.

The invention further relates to a polynucleotide encoding the polypeptide of the invention, and a nucleic acid construct or expression vector comprising a polynucleotide encoding a polypeptide of the invention, which is operably linked to one or more control sequences that direct the production of the polypeptide in an expression host. The invention further relates to a recombinant host cell comprising a polynucleotide encoding a polypeptide of the invention, which is operably linked to one or more control sequences that direct the production of the polypeptide, wherein the method may further comprise cultivating a cell, which in its wild-type form produces the polypeptide, under conditions conducive for production of the polypeptide and optionally recovering the polypeptide. The invention also relates to a method of producing a polypeptide having DNase activity, comprising cultivating a recombinant host cell comprising a polynucleotide encoding the polypeptide under conditions conducive for production of the polypeptide.

Overview of Sequences
SEQ ID NO 1 DNA encoding full length polypeptide from *Streptomyces* sp-63712
SEQ ID NO 2 polypeptide derived from SEQ ID NO 1
SEQ ID NO 3 mature polypeptide obtained from *Streptomyces* sp-63712

SEQ ID NO 4 DNA encoding full length polypeptide from *Saccharothrix australiensis*
SEQ ID NO 5 polypeptide derived from SEQ ID NO 4
SEQ ID NO 6 mature polypeptide obtained from *Saccharothrix australiensis*
SEQ ID NO 7 DNA encoding full length polypeptide from *Kutzneria albida*
SEQ ID NO 8 polypeptide derived from SEQ ID NO 7
SEQ ID NO 9 mature polypeptide obtained from *Kutzneria albida*
SEQ ID NO 10 histidine tail
SEQ ID NOs 11-17 are motifs disclosed herein.

Definitions

The term "DNase" means a polypeptide with DNase activity that catalyzes the hydrolytic cleavage of phosphodiester linkages in the DNA backbone, thus degrading DNA. The term "DNases" and the expression "a polypeptide with DNase activity" are used interchangeably throughout the application. For purposes of the present invention, DNase activity is determined according to the procedure described in Assay I or Assay II. In one aspect, the polypeptide of the present invention has at least 20%, e.g., at least 40%, at least 50%, at least 60%, at least 70%, at least 80%, at least 90%, at least 95%, or at least 100% of the DNase activity of the mature polypeptide shown in SEQ ID NO: 3, SEQ ID NO: 6 or SEQ ID NO: 9

The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The term "biofilm" means organic matter produced by any group of microorganisms in which cells stick to each other or stick to a surface, such as a textile, dishware or hard surface or another kind of surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces. The microbial cells growing in a biofilm are physiologically distinct from planktonic cells of the same organism, which, by contrast, are single-cells that may float or swim in a liquid medium. Bacteria living in a biofilm usually have significantly different properties from planktonic bacteria of the same species, as the dense and protected environment of the film allows them to cooperate and interact in various ways. One benefit of this environment for the microorganisms is increased resistance to detergents and antibiotics, as the dense extracellular matrix and the outer layer of cells protect the interior of the community. On laundry biofilm producing bacteria can be found among the following species including *Acinetobacter* sp., *Aeromicrobium* sp., *Brevundimonas* sp., *Microbacterium* sp., *Micrococcus luteus, Pseudomonas* sp., *Staphylococcus epidermidis*, and *Stenotrophomonas* sp. On hard surfaces biofilm producing bacteria can be found among the following species: *Acinetobacter* sp., *Aeromicrobium* sp., *Brevundimonas* sp., *Microbacterium* sp., *Micrococcus luteus, Pseudomonas* sp., *Staphylococcus epidermidis, Staphylococcus aureus* and *Stenotrophomonas* sp.

The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

The term "eDNA" means in the present context extracellular DNA.

The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

The term "deep cleaning" means disruption, reduction or removal of organic components such as polysaccharides, proteins, DNA, soil or other components present in organic matter such as biofilm.

The term "detergent adjunct ingredient" is different to the DNases of this invention. The precise nature of these additional adjunct components, and levels of incorporation thereof, will depend on the physical form of the composition and the nature of the operation for which it is to be used. Suitable adjunct materials include, but are not limited to the components described below such as surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric agents, clay soil removal/anti-redeposition agents, brighteners, suds suppressors, dyes, perfumes, structure elasticizing agents, fabric softeners, carriers, hydrotropes, builders and co-builders, fabric huing agents, anti-foaming agents, dispersants, processing aids, and/or pigments.

The term "detergent composition" refers to compositions that find use in the removal of undesired compounds from items to be cleaned, such as textiles. The terms "detergent compositions" and "cleaning compositions" are used interchangeably in the present application. The detergent composition may be used to e.g. clean textiles for both household cleaning and industrial cleaning. The terms encompass any materials/compounds selected for the particular type of cleaning composition desired and the form of the product (e.g., liquid, gel, powder, granulate, paste, or spray compositions) and includes, but is not limited to, detergent compositions (e.g., liquid and/or solid laundry detergents and fine fabric detergents; fabric fresheners; fabric softeners; and textile and laundry pre-spotters/pretreatment). In addition to containing the enzyme of the invention, the detergent formulation may contain one or more additional enzymes (such as proteases, amylases, lipases, cutinases, cellulases, endoglucanases, xyloglucanases, pectinases, pectin lyases, xanthanases, peroxidases, haloperoxygenases, catalases and mannanases, or any mixture thereof), and/or detergent adjunct ingredients such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

The term "expression" includes any step involved in the production of a polypeptide including, but not limited to, transcription, post-transcriptional modification, translation, post-translational modification, and secretion.

The term "expression vector" means a linear or circular DNA molecule that comprises a polynucleotide encoding a polypeptide and is operably linked to control sequences that provide for its expression. A control sequence may be foreign or heterologous to the expression vector.

A "His-tag" refers to a polyhistidine tag typically comprising at least 6 histidine residues, that may be added to the N- or C-terminal. His-tags are known in the art for use in e.g. protein purification, but may also be used for improving solubility at low pH values. Similarly, an "HQ-tag", i.e. a histidine-glutamine tag, may also be used for the purpose of purification as is known in the art.

The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). An isolated substance may be present in a fermentation broth sample; e.g. a host cell may be genetically modified to express the polypeptide of the invention. The fermentation broth from that host cell will comprise the isolated polypeptide.

The term "laundering" relates to both household laundering and industrial laundering and means the process of treating textiles with a solution containing a cleaning or detergent composition of the present invention. The laundering process can for example be carried out using e.g. a household or an industrial washing machine or can be carried out by hand.

By the term "malodor" is meant an odor which is not desired on clean items. The cleaned item should smell fresh and clean without malodors adhered to the item. One example of malodor is compounds with an unpleasant smell, which may be produced by microorganisms and trapped within a biofilm or stick to the "glue" of a biofilm. Other examples of unpleasant smells are sweat or body odor adhered to an item, which has been in contact with human or animal. Other examples of malodor are odor from spices, which sticks to items for example curry or other exotic spices which smells strongly.

The term "mature polypeptide" means a polypeptide in its final form following translation and any post-translational modifications, such as N-terminal processing, C-terminal truncation, glycosylation, phosphorylation, etc.

In one aspect, the mature polypeptide is amino acids 1 to 182 of SEQ ID NO: 2. Amino acids −32 to −1 of SEQ ID NO: 2 is the signal peptide.

In one aspect, the mature polypeptide is amino acids 1 to 182 of SEQ ID NO: 5. Amino acids −27 to −1 of SEQ ID NO: 5 is the signal peptide.

In one aspect, the mature polypeptide is amino acids 1 to 182 of SEQ ID NO: 8. Amino acids −30 to −1 of SEQ ID NO: 8 is the signal peptide.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

The term "mature polypeptide coding sequence" means a polynucleotide that encodes a mature polypeptide having DNase activity.

In one aspect, the mature polypeptide coding sequence is nucleotides 97 to 642 of SEQ ID NO: 1 and nucleotides 1 to 96 of SEQ ID NO: 1 encode a signal peptide.

In one aspect, the mature polypeptide coding sequence is nucleotides 82 to 627 of SEQ ID NO: 4 and nucleotides 1 to 81 of SEQ ID NO: 4 encode a signal peptide.

In one aspect, the mature polypeptide coding sequence is nucleotides 91 to 636 of SEQ ID NO: 7 and nucleotides 1 to 90 of SEQ ID NO: 7 encode a signal peptide.

The term "nucleic acid construct" means a nucleic acid molecule, either single- or double-stranded, which is isolated from a naturally occurring gene or is modified to contain segments of nucleic acids in a manner that would not otherwise exist in nature or which is synthetic, and which comprises one or more control sequences that may be heterologous.

The term "operably linked" means a configuration in which a control sequence is placed at an appropriate position relative to the coding sequence of a polynucleotide such that the control sequence directs expression of the coding sequence.

The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment−
Total Number of Gaps in Alignment)

The term "variant" means a polypeptide having DNase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Nomenclature

For purposes of the present invention, the nomenclature [E/Q] means that the amino acid at this position may be a glutamic acid (Glu, E) or a glutamine (Gln, Q). Likewise, the nomenclature [V/G/A/I] means that the amino acid at this position may be a valine (Val, V), glycine (Gly, G), alanine (Ala, A) or isoleucine (Ile, I), and so forth for other combinations as described herein. Unless otherwise limited further, the amino acid X is defined such that it may be any of the 20 natural amino acids.

BRIEF DESCRIPTION OF THE DRAWING

FIG. 1 shows and alignment of the polypeptides of SEQ ID NOs. 3, 6 and 9.

DETAILED DESCRIPTION OF THE INVENTION

The present invention relates to novel polypeptides having deoxyribonuclease (DNase) activity which can be used for preventing, reducing or removing biofilm soiling on items such as textiles and/or fabric. A polypeptide having DNase activity or a deoxyribonuclease (DNase) is any enzyme that catalyzes the hydrolytic cleavage of phosphodiester linkages in the DNA backbone, thus degrading DNA. The two terms polypeptide having DNase activity and DNase are used interchangeably.

Polypeptides Having DNase Activity

The present invention relates to polypeptides having DNase activity i.e. DNases. Examples of polypeptides having DNase activity are polypeptides comprising the PFAM domain DUF1524 (http://pfam.xfam.org/), "The Pfam protein families database: towards a more sustainable future", R. D. Finn, et. al. Nucleic Acids Research (2016) Database Issue 44: D279-D285". The DUF1524 domain contains a conserved HXXP sequence motif commonly found in nucleases (M. A. Machnicka, et. al. Phylogenomics and sequence-structure-function relationships in the GmrSD family of Type IV restriction enzymes, BMC Bioinformatics, 2015, 16, 336). DUF means domain of unknown function, and the polypeptide families comprising, e.g., DUF have been collected together in the Pfam database. The Pfam data base provides sequence alignments and hidden Markov models that define the collected protein domains. A protein domain is a conserved part of a given protein sequence. Each domain forms a compact three-dimensional structure which can be independently stable and folded. Many proteins consist of several structural domains. One domain may appear in a variety of different proteins.

One particular DUF may be identified using the prefix DUF followed by a number, e.g., 1524. The DUF1524 is a family of proteins all comprising the HXXP motif, where H is the amino acid histidine, P is the amino acid proline and X is any amino acid. In one embodiment the polypeptides having DNase activity comprise the DUF1524 domain. Thus, according to one embodiment the invention relates to polypeptides having DNase activity, wherein the polypeptides comprise the DUF1524 domain. The invention also relates to the use of such DNases e.g. for cleaning of textiles and/or fabric. The invention further relates to compositions comprising polypeptides having DNase activity, and which comprise a DUF1524 domain e.g. HXXP. Such compositions may be but are not limited to liquid or powder laundry compositions, tablets, unit dose, spray or soap bars. Polypeptides comprising the DUF1524 domain comprise several motifs, of which one example is [E/D/H]H[I/V/L/F/M]X[P/A/S] (SEQ ID NO 11), situated in positions corresponding to positions 89 to 93 in *Kutzneria albida* (SEQ ID NO 9). H90 is a catalytic residue involved in the catalytic activity of DUF1524, and part of the HXXP motif.

As already described the polypeptides of the invention having DNase activity may comprise the structural domains of DUF1524. A further domain, preferably shared by the DNases of the invention, was identified. This domain is termed NUC1 and polypeptides of this domain are in addition to having DNase activity, characterized by comprising certain motifs, e.g. one or more of the motifs [F/L/Y/I]A[N/R]D[L/I/P/V] (SEQ ID NO: 12), corresponding to position 113 to 117 in SEQ ID NO 9 or C[DIN]T[A/R] (SEQ ID NO: 13), corresponding to position 44 to 47 in SEQ ID NO 9. From the NUC1 domain a sub-domain has been identified by the inventors and this domain is termed the NUC1_A domain. In addition to comprising any of the domains above the polypeptides having DNase activity belonging to the NUC1_A domain may share the common motif [D/Q][I/V]DH (SEQ ID NO 14), corresponding to amino acid 87 to 90 in the reference polypeptide (SEQ ID NO: 9). The D at the position corresponding to position 89 of SEQ ID NO 9 is predicted to be involved in binding of catalytic metal ion cofactor. In one embodiment the invention relates to polypeptides comprising the motif [D/Q][I/V]DH (SEQ ID NO: 14), wherein the polypeptides have DNase activity. In one embodiment the invention relates to polypeptides comprising the motif [D/Q][I/V]DH (SEQ ID NO: 14). In some embodiments of the invention the DNases of the invention belong to a specific subgroup or clade comprising the motif C[DN]TRE (SEQ ID NO 15) corresponding to positions 44 to 48 of SEQ ID NO 9 and [DN]SAEK (SEQ ID NO 16), corresponding to positions 168 to 172 of SEQ ID NO. In one aspect, the polypeptide of the invention having DNase activity belongs to the CNTRE clade and comprises one or more motif(s) selected from C[DN]TRE (SEQ ID NO 15) and [DN]SAEK (SEQ ID NO 16. In one aspect, the polypeptide of the invention having DNase activity belongs to the CNTRE clade and comprises one or more of the motif(s) selected from C[DN]TRE (SEQ ID NO 15) and [DN]SAEK (SEQ ID NO 16), wherein the DNase is derived from bacteria e.g. is of bacterial origin. An alignment of the polypeptides of the invention comprised in the clades is shown in FIG. 1. The CNTRE clade is defined in the present context as a subgroup of NUC1_A DNases of bacterial origin which share the motifs C[DN]TRE (SEQ ID NO 15) and [DN]SAEK (SEQ ID NO 16) and is structurally and optionally also functionally more related than other NUC1_A DNases, i.e. it is a subgroup of closely related DNases. In one aspect, the invention relates to a polypeptide having DNase activity, wherein the polypeptide belongs to the CNTRE clade and comprises one or more motif(s) selected from C[DN]TRE (SEQ ID NO 15) and [DN]SAEK (SEQ ID NO 16), wherein the DNase is a bacterial DNase i.e. of bacterial origin. In one aspect, the invention relates to a polypeptide having DNase activity, wherein the polypeptide belongs to the CNTRE clade and comprises one or more motif(s) selected from C[DN]TRE (SEQ ID NO 15) and [DN]SAEK (SEQ ID NO 16) and wherein the polypeptide is selected from the group consisting of in SEQ ID NO: 3, SEQ ID NO: 6 and SEQ ID NO: 9. In one aspect of the invention the DNase is a polypeptide comprising one of more of the motifs selected from the group consisting of [E/D/H]H[I/V/L/F/M]X[P/A/S] (SEQ ID NO 11), [F/L/Y/I]A[N/R]D[L/I/P/V] (SEQ ID NO: 12), C[D/N]T[A/R] (SEQ ID NO 13), [D/Q][I/V]DH (SEQ ID NO 14), C[DN]TRE (SEQ ID NO 15) and [DN]SAEK (SEQ ID NO 16). Preferably, the DNases of the invention comprises one or all motif(s) C[DN]TRE (SEQ ID NO 15) and [DN]SAEK (SEQ ID NO 16), and are of bacterial origin. One embodiment of the invention relates to a polypeptide having DNase activity, wherein the polypeptide comprises any of the motifs [E/D/H]H[I/V/L/F/M]X[P/A/S] (SEQ ID NO 11), [T/D/S][G/N]PQL (SEQ ID NO: 11), [F/L/Y/I]A[N/R]D[L/I/P/V] (SEQ ID NO: 12), C[DIN]T[A/R](SEQ ID NO 13), [D/Q][I/V]DH (SEQ ID NO 14), C[DN]TRE (SEQ ID NO 15), [DN]SAEK (SEQ ID NO 16) and wherein the polypeptide is selected from the group consisting of:
  i) a polypeptide comprising or consisting of SEQ ID NO 3 or a polypeptide having at least 80% sequence identity hereto;
  ii) a polypeptide comprising or consisting of SEQ ID NO 6 or a polypeptide having at least 80% sequence identity hereto; and
  iii) a polypeptide comprising or consisting of SEQ ID NO 9 or a polypeptide having at least 80% sequence identity hereto;

In one embodiment, the DNase polypeptide comprises one or more of the motif(s) C[DN]TRE (SEQ ID NO 15) and [DN]SAEK (SEQ ID NO 16) and preferably is selected from the group of polypeptides comprising the amino acid sequences shown in SEQ ID NO: 3, SEQ ID NO: 6 and SEQ ID NO: 9 or polypeptides having at least 80% sequence identity hereto.

It is well known that DNases deriving from organisms may share common structural elements, which can be identified by comparing the primary structures e.g. amino acid sequences and grouping the DNases according to sequence homology. However, common structural elements may also be identified by comparing the three-dimensional (3D) structure of various DNases. Both approaches have been applied in the present invention.

The structural approach identified DNases which derive from organisms from divergent taxonomic groups but share structural elements common for the identified group. A clade is a grouping that includes a common ancestor and all the descendants (living and extinct) of that ancestor (http://evolution.berkeley.edu/evolibrary/article/0_0_0/evo_06) a clade has a shared phylogeny. In the examples is described building of phylogenetic trees, such trees have branches which represent clades, see FIG. 1.

One embodiment of the invention relates a polypeptide of the CNTRE clade, wherein the polypeptide has DNase activity, and wherein the polypeptide is selected from the group consisting of:
  (a) a polypeptide having at least 80% sequence identity to the polypeptide of SEQ ID NO: 3;
  (b) a polypeptide having at least 80% sequence identity to the polypeptide of SEQ ID NO: 6;
  (c) a polypeptide having at least 80% sequence identity to the polypeptide of SEQ ID NO: 9;
  (d) a variant of the polypeptide selected from the group consisting of SEQ ID NO: 3, SEQ ID NO: 6 and SEQ ID NO: 9, wherein the variant has DNase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions;
  (e) a polypeptide comprising the polypeptide of (a) to (d) and a N-terminal and/or C-terminal His-tag and/or HQ-tag;
  (f) a polypeptide comprising the polypeptide of (a) to (d) and a N-terminal and/or C-terminal extension of between 1 and 10 amino acids; and
  (g) a fragment of the polypeptide of (a) to (d) having DNase activity and having at least 90% of the length of the mature polypeptide
  (h) a polypeptide of bacterial origin comprising one or both the motif(s) C[DN]TRE (SEQ ID NO 15), and [DN]SAEK (SEQ ID NO 16).

The DNases of the present invention are useful in cleaning compositions and are effective in deep cleaning of surfaces such as fabrics. The DNases of the present invention are effective in reducing or removing DNA soiling from e.g. organic matter. One example of organic matter is biofilm which is an extracellular matrix produced by various microorganisms. The extracellular polymeric matrix is composed of polysaccharides, extracellular DNA and proteins. Organic matter like biofilm may be sticky or gluing, which when present on textile may give rise to redeposition or backstaining of soil resulting in a greying of the textile. Another drawback of organic matter is malodor as various malodor related molecules are often associated with organic matter e.g. biofilm. One aspect of the invention relates to a method for laundering an item comprising the steps of:
  a. Exposing an item to a wash liquor comprising a polypeptide or a cleaning composition comprising a polypeptide selected from the group consisting of SEQ ID NO: 3, SEQ ID NO: 6 and SEQ ID NO: 9 or polypeptides having at least 80% sequence identity hereto, wherein the polypeptide has DNase activity;
  b. Completing at least one wash cycle; and
  c. Optionally rinsing the item,
  wherein the item is a textile.

The DNases of the invention are therefore useful for prevention, reduction or removal of malodor and for prevention, reduction of redeposition and improving whiteness.

One embodiment of the invention relates to the use of polypeptide selected from the group consisting of SEQ ID NO: 3, SEQ ID NO: 6 and SEQ ID NO: 9 or polypeptides having at least 80% sequence identity hereto for deep cleaning of an item, wherein the item is a textile. Another embodiment relates to the use of polypeptide selected from the group consisting of SEQ ID NO: 3, SEQ ID NO: 6 and SEQ ID NO: 9 or polypeptides having at least 80% sequence identity hereto;
  (i) for preventing, reducing or removing stickiness of the item;
  (ii) for pretreating stains on the item;
  (iii) for preventing, reducing or removing redeposition of soil during a wash cycle;
  (iv) for preventing, reducing or removing adherence of soil to the item;
  (v) for maintaining or improving whiteness of the item;

(vi) for preventing, reducing or removal malodor from the item,
wherein the item is a textile.

The textile may e.g. be cotton or polyester or a mixture hereof.

One embodiment of the invention relates to a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 3, SEQ ID NO: 6 or SEQ ID NO: 9.

In one embodiment, the present invention relates to polypeptides having a sequence identity to the mature polypeptide of SEQ ID NO: 2 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the DNase activity of the mature polypeptide of SEQ ID NO: 2, e.g. at least 80% or at least 90% of the DNase activity of the mature polypeptide of SEQ ID NO: 2.

In a particular embodiment the invention relates to polypeptides having a sequence identity to the mature polypeptide of SEQ ID NO: 5 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the DNase activity of the mature polypeptide of SEQ ID NO: 5, e.g. at least 80% or at least 90% of the DNase activity of the mature polypeptide of SEQ ID NO: 5.

In a particular embodiment the invention relates to polypeptides having a sequence identity to the mature polypeptide of SEQ ID NO: 8 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the DNase activity of the mature polypeptide of SEQ ID NO: 8, e.g. at least 80% or at least 90% of the DNase activity of the mature polypeptide of SEQ ID NO: 8.

In some embodiments, the polypeptide has been isolated. A polypeptide of the present invention preferably comprises or consists of the amino acid sequence shown in SEQ ID NO: 3 or an allelic variant thereof; or is a fragment thereof having DNase activity. In another aspect, the polypeptide comprises or consists of the mature polypeptide of SEQ ID NO: 2. In another aspect, the polypeptide comprises or consists of amino acids 1 to 182 of SEQ ID NO: 2.

In one embodiment, the polypeptide preferably comprises or consists of the amino acid sequence shown in SEQ ID NO: 3; comprises the amino acid sequence shown in SEQ ID NO: 3 and a N-terminal and/or C-terminal His-tag and/or HQ-tag; comprises the amino acid sequence of SEQ ID NO: 3 and a N-terminal and/or C-terminal extension of between 1 and 10 amino acids; or is a fragment thereof having DNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 3.

In some embodiments, the polypeptide has been isolated. A polypeptide of the present invention preferably comprises or consists of the amino acid sequence shown in SEQ ID NO: 6 or an allelic variant thereof; or is a fragment thereof having DNase activity. In another aspect, the polypeptide comprises or consists of the mature polypeptide of SEQ ID NO: 5. In another aspect, the polypeptide comprises or consists of amino acids 1 to 182 of SEQ ID NO: 5.

In one embodiment, the polypeptide preferably comprises or consists of the amino acid sequence shown in SEQ ID NO: 6; comprises the amino acid sequence shown in SEQ ID NO: 6 and a N-terminal and/or C-terminal His-tag and/or HQ-tag; comprises the amino acid sequence of SEQ ID NO: 6 and a N-terminal and/or C-terminal extension of between 1 and 10 amino acids; or is a fragment thereof having DNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 6.

In some embodiments, the polypeptide has been isolated. A polypeptide of the present invention preferably comprises or consists of the amino acid sequence shown in SEQ ID NO: 9 or an allelic variant thereof; or is a fragment thereof having DNase activity. In another aspect, the polypeptide comprises or consists of the mature polypeptide of SEQ ID NO: 8. In another aspect, the polypeptide comprises or consists of amino acids 1 to 182 of SEQ ID NO: 8.

In one embodiment, the polypeptide preferably comprises or consists of the amino acid sequence shown in SEQ ID NO: 9; comprises the amino acid sequence shown in SEQ ID NO: 9 and a N-terminal and/or C-terminal His-tag and/or HQ-tag; comprises the amino acid sequence of SEQ ID NO: 9 and a N-terminal and/or C-terminal extension of between 1 and 10 amino acids; or is a fragment thereof having DNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 9.

In some embodiments, the present invention relates to variants of the mature polypeptide shown in SEQ ID NO: 3 comprising a substitution, deletion, and/or insertion at one or more (e.g., several) positions. In some embodiments, the number of amino acid substitutions, deletions and/or insertions introduced into the mature polypeptide shown in SEQ ID NO: 3 is up to 10, e.g., 1, 2, 3, 4, 5, 6, 7, 8, 9, or 10.

In some embodiments, the present invention relates to variants of the mature polypeptide shown in SEQ ID NO: 6 comprising a substitution, deletion, and/or insertion at one or more (e.g., several) positions. In some embodiments, the number of amino acid substitutions, deletions and/or insertions introduced into the mature polypeptide shown in SEQ ID NO: 6 is up to 10, e.g., 1, 2, 3, 4, 5, 6, 7, 8, 9, or 10.

In some embodiments, the present invention relates to variants of the mature polypeptide shown in SEQ ID NO: 9 comprising a substitution, deletion, and/or insertion at one or more (e.g., several) positions. In some embodiments, the number of amino acid substitutions, deletions and/or insertions introduced into the mature polypeptide shown in SEQ ID NO: 9 is up to 10, e.g., 1, 2, 3, 4, 5, 6, 7, 8, 9, or 10.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant molecules are tested for DNase activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, EMBO J. 12: 2575-2583; Dawson et al., 1994, Science 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, J. Ind. Microbiol. Biotechnol. 3: 568-576; Svetina et al., 2000, J. Biotechnol. 76: 245-251; Rasmussen-Wilson et al., 1997, Appl. Environ. Microbiol. 63: 3488-3493; Ward et al., 1995, Biotechnology 13: 498-503; and Contreras et al., 1991, Biotechnology 9: 378-381; Eaton et al., 1986, Biochemistry 25: 505-512; Collins-Racie et al., 1995, Biotechnology 13: 982-987; Carter et al., 1989, Proteins: Structure, Function, and Genetics 6: 240-248; and Stevens, 2003, Drug Discovery World 4: 35-48.

Sources of Polypeptides Having DNase Activity

A polypeptide having DNase activity of the present invention may be obtained from microorganisms of any genus, e.g. a bacterial genus such as from the phylum Actinobacteria. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularty.

In one aspect, the polypeptide is a Streptomyces polypeptide, e.g., a polypeptide obtained from Streptomyces sp-63712.

In one aspect, the polypeptide is a Saccharothrix polypeptide, e.g., a polypeptide obtained from Saccharothrix australiensis In one aspect, the polypeptide is a Kutzneria polypeptide, e.g., a polypeptide obtained from Kutzneria albida.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to polynucleotides encoding a polypeptide of the present invention, as described herein. In some embodiments, the polynucleotide encoding the polypeptide of the present invention has been isolated.

In one embodiment, the present invention relates to a polynucleotide encoding a polypeptide having DNase activity, wherein the polynucleotide having a sequence identity to the mature polypeptide coding sequence of SEQ ID NO: 1 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having DNase activity, wherein the polynucleotide having a sequence identity to the mature polypeptide coding sequence of SEQ ID NO: 4 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having DNase activity, wherein the polynucleotide having a sequence identity to the mature polypeptide coding sequence of SEQ ID NO: 7 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences. The control sequence may be heterologous to the host cell.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including variant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and variant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), Bacillus licheniformis alpha-amylase (amyL), and Escherichia coli ribosomal RNA (rmB).

Preferred terminators for filamentous fungal host cells are obtained from the genes for Aspergillus nidulans acetamidase, Aspergillus nidulans anthranilate synthase, Aspergillus niger glucoamylase, Aspergillus niger alpha-glucosidase, Aspergillus oryzae TAKA amylase, Fusarium oxysporum trypsin-like protease, Trichoderma reesei beta-glucosidase, Trichoderma reesei cellobiohydrolase I, Trichoderma reesei cellobiohydrolase II, Trichoderma reesei endoglucanase I, Trichoderma reesei endoglucanase II, Trichoderma reesei endoglucanase III, Trichoderma reesei endoglucanase V, Trichoderma reesei xylanase I, Trichoderma reesei xylanase II, Trichoderma reesei xylanase III, Trichoderma reesei beta-xylosidase, and Trichoderma reesei translation elongation factor.

Preferred terminators for yeast host cells are obtained from the genes for Saccharomyces cerevisiae enolase, Saccharomyces cerevisiae cytochrome C (CYC1), and Saccharomyces cerevisiae glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a Bacillus thuringiensis cryIIIA gene (WO 94/25612) and a Bacillus subtilis SP82 gene (Hue et al., 1995, Journal of Bacteriology 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for Aspergillus oryzae TAKA amylase and Aspergillus nidulans triose phosphate isomerase.

Suitable leaders for yeast host cells are obtained from the genes for Saccharomyces cerevisiae enolase (ENO-1), Saccharomyces cerevisiae 3-phosphoglycerate kinase, Saccharomyces cerevisiae alpha-factor, and Saccharomyces cerevisiae alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for Aspergillus nidulans anthranilate synthase, Aspergillus niger glucoamylase, Aspergillus niger alpha-glucosidase Aspergillus oryzae TAKA amylase, and Fusarium oxysporum trypsin-like protease.

Useful polyadenylation sequences for yeast host cells are described by Guo and Sherman, 1995, Mol. Cellular Biol. 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for Bacillus NCIB 11837 maltogenic amylase, Bacillus licheniformis subtilisin, Bacillus licheniformis beta-lactamase, Bacillus stearothermophilus alpha-amylase, Bacillus stearothermophilus neutral proteases (nprT, nprS, nprM), and Bacillus subtilis prsA. Further signal peptides are described by Simonen and Palva, 1993, Microbiological Reviews 57: 109-137.

Effective signal peptide coding sequences for filamentous fungal host cells are the signal peptide coding sequences obtained from the genes for Aspergillus niger neutral amylase, Aspergillus niger glucoamylase, Aspergillus oryzae TAKA amylase, Humicola insolens cellulase, Humicola insolens endoglucanase V, Humicola lanuginosa lipase, and Rhizomucor miehei aspartic proteinase.

Useful signal peptides for yeast host cells are obtained from the genes for Saccharomyces cerevisiae alpha-factor and Saccharomyces cerevisiae invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for Bacillus subtilis alkaline protease (aprE), Bacillus subtilis neutral protease (nprT), Myceliophthora thermophila laccase (WO 95/33836), Rhizomucor miehei aspartic proteinase, and Saccharomyces cerevisiae alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the Aspergillus niger glucoamylase promoter, Aspergillus oryzae TAKA alpha-amylase promoter, and Aspergillus oryzae glucoamylase promoter, Trichoderma reesei cellobiohydrolase I promoter, and Trichoderma reesei cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences, which may be heterologous to each other, may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome.

The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMß1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. The control sequence(s) may be heterologous to the host cell. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, Bacillus, Clostridium, Enterococcus, Geobacillus, Lactobacillus, Lactococcus, Oceanobacillus, Staphylococcus, Streptococcus, and Streptomyces. Gram-negative bacteria include, but are not limited to, Campylobacter, E. coli, Flavobacterium, Fusobacterium, Helicobacter, Ilyobacter, Neisseria, Pseudomonas, Salmonella, and Ureaplasma.

The bacterial host cell may be any Bacillus cell including, but not limited to, Bacillus alkalophilus, Bacillus altitudinis, Bacillus amyloliquefaciens, B. amyloliquefaciens subsp. plantarum, Bacillus brevis, Bacillus circulans, Bacillus dausii, Bacillus coagulans, Bacillus firmnnus, Bacillus lautus, Bacillus lentus, Bacillus licheniformis, Bacillus megaterium, Bacillus methylotrophicus, Bacillus pumilus, Bacillus safensis, Bacillus stearothermophilus, Bacillus subtilis, and Bacillus thuringiensis cells.

The bacterial host cell may also be any Streptococcus cell including, but not limited to, Streptococcus equisimilis, Streptococcus pyogenes, Streptococcus uberis, and Streptococcus equi subsp. Zooepidemicus cells.

The bacterial host cell may also be any Streptomyces cell including, but not limited to, Streptomyces achromogenes, Streptomyces avermitilis, Streptomyces coelicolor, Streptomyces griseus, and Streptomyces lividans cells.

The introduction of DNA into a Bacillus cell may be effected by protoplast transformation (see, e.g., Chang and Cohen, 1979, Mol. Gen. Genet. 168: 111-115), competent cell transformation (see, e.g., Young and Spizizen, 1961, J. Bacteriol. 81: 823-829, or Dubnau and Davidoff-Abelson, 1971, J. Mol. Biol. 56: 209-221), electroporation (see, e.g., Shigekawa and Dower, 1988, Biotechniques 6: 742-751), or conjugation (see, e.g., Koehler and Thorne, 1987, J. Bacteriol. 169: 5271-5278). The introduction of DNA into an E. coli cell may be effected by protoplast transformation (see, e.g., Hanahan, 1983, J. Mol. Biol. 166: 557-580) or electroporation (see, e.g., Dower et al., 1988, Nucleic Acids Res. 16: 6127-6145). The introduction of DNA into a Streptomyces cell may be effected by protoplast transformation, electroporation (see, e.g., Gong et al., 2004, Folia Microbiol. (Praha) 49: 399-405), conjugation (see, e.g., Mazodier et al., 1989, J. Bacteriol. 171: 3583-3585), or transduction (see, e.g., Burke et al., 2001, Proc. Natl. Acad. Sci. USA 98: 6289-6294). The introduction of DNA into a Pseudomonas cell may be effected by electroporation (see, e.g., Choi et al., 2006, J. Microbiol. Methods 64: 391-397) or conjugation (see, e.g., Pinedo and Smets, 2005, Appl. Environ. Microbiol. 71: 51-57). The introduction of DNA into a Streptococcus cell may be effected by natural competence (see, e.g., Perry and Kuramitsu, 1981, Infect. Immun. 32: 1295-1297), protoplast transformation (see, e.g., Catt and Jollick, 1991, Microbios 68: 189-207), electroporation (see, e.g., Buckley et al., 1999, Appl. Environ. Microbiol. 65: 3800-3804), or conjugation (see, e.g., Clewell, 1981, Microbiol. Rev. 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, Ainsworth and Bisby's Dictionary of The Fungi, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, Soc. App. Bacteriol. Symposium Series No. 9, 1980).

The yeast host cell may be a Candida, Hansenula, Kluyveromyces, Pichia, Saccharomyces, Schizosaccharomyces, or Yarrowia cell, such as a Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis, or Yarrowia lipolytica cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as Saccharomyces cerevisiae is by budding of a unicellular thallus and carbon catabolism may be fermentative.

The filamentous fungal host cell may be an Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes, or Trichoderma cell.

For example, the filamentous fungal host cell may be an Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium

*roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichodermna reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally, (b) recovering the polypeptide.

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides having DNase activity. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In some embodiments, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may, for example, be produced by a method described in WO 90/15861 or WO 2010/096673.

Enzyme Compositions

The invention relates to compositions comprising a DNase of the present invention in combination with one or more additional component(s). The choice of additional components is within the skill of the artisan and includes conventional ingredients, including the exemplary non-limiting components set forth below.

One embodiment of the invention relates to a composition comprising:
a) at least 0.001 ppm of at least one polypeptide having DNase activity, wherein the DNase is selected for the group consisting of: SEQ ID NO 3, SEQ ID NO 6, SEQ ID NO 9 and polypeptides having at least 80% sequence identity hereto;
b) one or more adjunct ingredient.

One embodiment of the invention relates to a cleaning composition comprising:
a) at least 0.001 ppm of at least one polypeptide having DNase activity, wherein the DNase is selected for the group consisting of: SEQ ID NO 3, SEQ ID NO 6, SEQ ID NO 9 and polypeptides having at least 80% sequence identity hereto;
b) one or more cleaning composition component, preferably selected from surfactants, builders, bleach components, polymers, dispersing agents and additional enzymes.

The choice of cleaning components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

Surfactants

The detergent composition may comprise one or more surfactants, which may be anionic and/or cationic and/or non-ionic and/or semi-polar and/or zwittenonic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and may include any conventional surfactant(s) known in the art.

When included therein the detergent will usually contain from about 1% to about 40% by weight of an anionic surfactant, such as from about 5% to about 30%, including from about 5% to about 15%, or from about 15% to about 20%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

When included therein the detergent will usually contain from about 1% to about 40% by weigh of a cationic surfactant, for example from about 0.5% to about 30%, in particular from about 1% to about 20%, from about 3% to about 10%, such as from about 3% to about 5%, from about 8% to about 12% or from about 10% to about 12%. Non-limiting examples of cationic surfactants include alkyldimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, ester quats, and combinations thereof.

When included therein the detergent will usually contain from about 0.2% to about 40% by weight of a nonionic surfactant, for example from about 0.5% to about 30%, in particular from about 1% to about 20%, from about 3% to about 10%, such as from about 3% to about 5%, from about 8% to about 12%, or from about 10% to about 12%. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof.

When included therein the detergent will usually contain from about 0.1% to about 10% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, and combinations thereof.

When included therein the detergent will usually contain from about 0.1% to about 10% by weight of a zwitterionic surfactant. Non-limiting examples of zwitterionic surfactants include betaines such as alkyidimethylbetaines, sulfobetaines, and combinations thereof.

Builders and Co-Builders

The detergent composition may contain about 0-65% by weight, such as about 5% to about 50% of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in cleaning detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as 2,2'-iminodiethan-1-ol), triethanolamine (TEA, also known as 2,2',2"-nitrilotriethan-1-ol), and (carboxymethyl)inulin (CMI), and combinations thereof.

The detergent composition may also contain 0-50% by weight, such as about 5% to about 30%, of a detergent co-builder. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra(methylenephosphonic acid) (EDTMPA), diethylenetriaminepentakis(methylenephosphonic acid) (DTMPA or DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taudne-N,N-diacetic acid (TUDA) and sulfomethyl-N,N-diacetic acid (SMDA), N-(2-hydroxyethyl)ethylenediamine-N,N',N"-triacetic acid (HEDTA), diethanoiglycine (DEG), diethylenetriamine penta(methylenephosphonic acid) (DTPMP), aminotris(methylenephosphonic acid) (ATMP), and combinations and salts thereof. Further exemplary builders and/or co-builders are described in, e.g., WO 09/102854, U.S. Pat. No. 5,977,053.

Bleaching Systems

The detergent may contain 0-30% by weight, such as about 1% to about 20%, of a bleaching system. Any bleaching system comprising components known in the art for use in cleaning detergents may be utilized. Suitable bleaching system components include sources of hydrogen peroxide; sources of peracids; and bleach catalysts or boosters.

Sources of Hydrogen Peroxide:

Suitable sources of hydrogen peroxide are inorganic persalts, including alkali metal salts such as sodium percarbonate and sodium perborates (usually mono- or tetrahydrate), and hydrogen peroxide-urea (1/1).

Sources of Peracids:

Peracids may be (a) incorporated directly as preformed peracids or (b) formed in situ in the wash liquor from hydrogen peroxide and a bleach activator (perhydrolysis) or (c) formed in situ in the wash liquor from hydrogen peroxide and a perhydrolase and a suitable substrate for the latter, e.g., an ester.

a) Suitable preformed peracids include, but are not limited to, peroxycarboxylic acids such as peroxybenzoic acid and its ring-substituted derivatives, peroxy-α-naphthoic acid, peroxyphthalic acid, peroxylauric acid, peroxystearic acid, ε-phthalimidoperoxycaproic acid [phthalimidoperoxyhexanoic acid (PAP)], and o-carboxybenzamidoperoxycaproic acid; aliphatic and aromatic diperoxydicarboxylic acids such as diperoxydodecanedioic acid, diperoxyazelaic acid, diperoxysebacic acid, diperoxybrassylic acid, 2-decyldiperoxybutanedioic acid, and diperoxyphthalic, -isophthalic and -terephthalic acids; perimidic acids; peroxymonosulfuric acid; peroxydisulfuric acid; peroxyphosphoric acid; peroxysilicic acid; and mixtures of said compounds. It is understood that the peracids mentioned may in some cases be best added as suitable salts, such as alkali metal salts (e.g., Oxone®) or alkaline earth-metal salts.

b) Suitable bleach activators include those belonging to the class of esters, amides, imides, nitriles or anhydrides and, where applicable, salts thereof. Suitable examples are tetraacetylethylenediamine (TAED), sodium 4-[(3,5,5-trimethylhexanoyl)oxy]benzene-1-sulfonate (ISONOBS), sodium 4-(dodecanoyloxy)benzene-1-sulfonate (LOBS), sodium 4-(decanoyloxy)benzene-1-sulfonate, 4-(decanoyloxy)benzoic acid (DOBA), sodium 4-(nonanoyloxy)benzene-1-sulfonate (NOBS), and/or those disclosed in WO98/17767. A particular family of bleach activators of interest was disclosed in EP624154 and particularly preferred in that family is acetyl triethyl citrate (ATC). ATC or a short chain triglyceride like triacetin has the advantage that they are environmentally friendly. Furthermore, acetyl triethyl citrate and triacetin have good hydrolytical stability in the product upon storage and are efficient bleach activators. Finally, ATC is multifunctional, as the citrate released in the perhydrolysis reaction may function as a builder.

Bleach Catalysts and Boosters

The bleaching system may also include a bleach catalyst or booster.

Some non-limiting examples of bleach catalysts that may be used in the compositions of the present invention include manganese oxalate, manganese acetate, manganese-collagen, cobalt-amine catalysts and manganese triazacyclononane (MnTACN) catalysts; particularly preferred are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Me3-TACN)Mn(O)3Mn(Me3-TACN)](PF6)2, and [2,2',2"-nitrilotris(ethane-1,2-diylazanylylidene-KN-methanylylidene)trphenolato-κ3O]manganese(III). The bleach catalysts may also be other metal compounds; such as iron or cobalt complexes.

In some embodiments, where a source of a peracid is included, an organic bleach catalyst or bleach booster may be used having one of the following formulae:

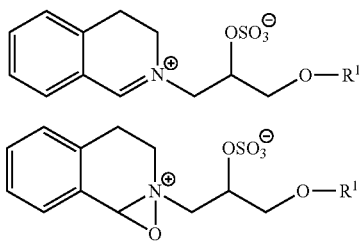

(iii) and mixtures thereof; wherein each R1 is independently a branched alkyl group containing from 9 to 24 carbons or linear alkyl group containing from 11 to 24 carbons, preferably each R1 is independently a branched alkyl group containing from 9 to 18 carbons or linear alkyl group containing from 11 to 18 carbons, more preferably each R1 is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl.

Other exemplary bleaching systems are described, e.g. in WO2007/087258, WO2007/087244, WO2007/087259, EP1867708 (Vitamin K) and WO2007/087242. Suitable photobleaches may for example be sulfonated zinc or aluminium pthalocyanines.

Metal Care Agents

Metal care agents may prevent or reduce the tarnishing, corrosion or oxidation of metals, including aluminium, stainless steel and non-ferrous metals, such as silver and copper. Suitable examples include one or more of the following:

(a) benzatriazoles, including benzotriazole or bis-benzotriazole and substituted derivatives thereof. Benzotriazole derivatives are those compounds in which the available substitution sites on the aromatic ring are partially or completely substituted. Suitable substituents include linear or branch-chain Ci-C20-alkyl groups (e.g., C1-C20-alkyl groups) and hydroxyl, thio, phenyl or halogen such as fluorine, chlorine, bromine and iodine.

(b) metal salts and complexes chosen from the group consisting of zinc, manganese, titanium, zirconium, hafnium, vanadium, cobalt, gallium and cerium salts and/or complexes, the metals being in one of the oxidation states II, III, IV, V or VI. In one aspect, suitable metal salts and/or metal complexes may be chosen from the group consisting of Mn(II) sulphate, Mn(II) citrate, Mn(II) stearate, Mn(II) acetylacetonate, K^TiF6 (e.g., K2TiF6), K^ZrF6 (e.g., K2ZrF6), CoSO4, Co(NOs)2 and Ce(NOs)3, zinc salts, for example zinc sulphate, hydrozincite or zinc acetate;

(c) silicates, including sodium or potassium silicate, sodium disilicate, sodium metasilicate, crystalline phyllosilicate and mixtures thereof.

Further suitable organic and inorganic redox-active substances that act as silver/copper corrosion inhibitors are disclosed in WO 94/26860 and WO 94/26859. Preferably the composition of the invention comprises from 0.1 to 5% by weight of the composition of a metal care agent, preferably the metal care agent is a zinc salt.

Hydrotropes

The detergent may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Polymers

The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or antifoaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly (ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomenc glycols, copolymers of poly(ethylene terephthalate) and poly (oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Suitable examples include PVP-K15, PVP-K30, ChromaBond S-400, ChromaBond S-403E and Chromabond S-100 from Ashland Aqualon, and Sokalan® HP 165, Sokalan® HP 50 (Dispersing agent), Sokalan® HP 53 (Dispersing agent), Sokalan® HP 59 (Dispersing agent), Sokalan® HP 56 (dye transfer inhibitor), Sokalan® HP 66 K (dye transfer inhibitor) from BASF. Further exemplary polymers include sulfonated polycarboxylates, polyethylene oxide and polypropylene oxide (PEO-PPO) and diquatemium ethoxy sulfate. Other exemplary polymers are disclosed in, e.g., WO 2006/130575. Salts of the above-mentioned polymers are also contemplated. Particularly preferred polymer is ethoxylated homopolymer Sokalan® HP 20 from BASF, which helps to prevent redeposition of soil in the wash liquor.

Fabric Hueing Agents

The detergent compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO2007/087243.

Enzymes

The detergent additive as well as the detergent composition may comprise one or more additional enzymes such as one or more lipase, cutinase, an amylase, carbohydrase, cellulase, pectinase, mannanase, arabinase, galactanase, xylanase, oxidase, e.g., a laccase, and/or peroxidase.

In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO99/001544.

Other cellulases are endo-beta-1,4-glucanase enzyme having a sequence of at least 97% identity to the amino acid sequence of position 1 to position 773 of SEQ ID NO:2 of WO 2002/099091 or a family 44 xyloglucanase, which a xyloglucanase enzyme having a sequence of at least 60% identity to positions 40-559 of SEQ ID NO: 2 of WO 2001/062903.

Commercially available cellulases include Celluzyme™, and Carezyme™ (Novozymes A/S) Carezyme Premium™ (Novozymes A/S), Celluclean™ (Novozymes A/S), Celluclean Classic™ (Novozymes A/S), Cellusoft™ (Novozymes AS), Whitezyme™ (Novozymes A/S), Clazinase™, and Puradax HA™ (Genencor International Inc.), and KAC-500(B)™ (Kao Corporation).

Mannanases

Suitable mannanases include those of bacterial or fungal origin. Chemically or genetically modified mutants are included. The mannanase may be an alkaline mannanase of Family 5 or 26. It may be a wild-type from *Bacillus* or *Humicola*, particularly *B. agaradhaerens, B. licheniformis, B. halodurans, B. clausii*, or *H. insolens*. Suitable mannanases are described in WO 1999/064619. A commercially available mannanase is Mannaway (Novozymes A/S).

Peroxidases/Oxidases

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include Guardzyme™ (Novozymes A/S).

Lipases and Cutinases:

Suitable lipases and cutinases include those of bacterial or fungal origin. Chemically modified or protein engineered mutant enzymes are included. Examples include lipase from *Thermomyces*, e.g. from *T. lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), *P.* sp. strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomonas mendocina* (U.S. Pat. No. 5,389,536), lipase from *Thermobifida fusca* (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and variants of the *M. smegmatis* perhydrolase in particular the S54V variant used in the commercial product Gentle Power Bleach from Huntsman Textile Effects Pte Ltd (WO10/100028).

Amylases:

Suitable amylases include alpha-amylases and/or a glucoamylases and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 are those having the substitutions:

M197T;
H156Y+A181T+N190F+A209V+Q264S; or
G48A+T49I+G107A+H156Y+A181T+N190F+I201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/023873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;
N128C+K178L+T182G+F202Y+Y305R+D319T+G475K;
S125A+N128C+K178L+T182G+Y305R+G475K; or
S125A+N28C+T131I+T165I+K178L+T182G+Y305R+G475K wherein the variants are C-terminally truncated and optionally further comprises a substitution at position 243 and/or a deletion at position 180 and/or position 181.

Further suitable amylases are amylases having SEQ ID NO: 1 of WO13184577 or variants having 90% sequence identity to SEQ ID NO: 1 thereof. Preferred variants of SEQ ID NO: 1 are those having a substitution, a deletion or an insertion in one of more of the following positions: K176, R178, G179, T180, G181, E187, N192, M199, I203, S241, R458, T459, D460, G476 and G477. More preferred variants of SEQ ID NO: 1 are those having the substitution in one of more of the following positions: K176L, E187P, N192FYH, M199L, I203YF, S241QADN, R458N, T459S, D460T, G476K and G477K and/or deletion in position R178 and/or S179 or of T180 and/or G181. Most preferred amylase variants of SEQ ID NO: 1 are those having the substitutions:

E187P+I203Y+G476K
E187P+I203Y+R458N+T459S+D460T+G476K wherein the variants optionally further comprise a substitution at position 241 and/or a deletion at position 178 and/or position 179.

Further suitable amylases are amylases having SEQ ID NO: 1 of WO10104675 or variants having 90% sequence identity to SEQ ID NO: 1 thereof. Preferred variants of SEQ ID NO: 1 are those having a substitution, a deletion or an insertion in one of more of the following positions: N21, D97, V128 K177, R179, S180, I181, G182, M200, L204, E242, G477 and G478. More preferred variants of SEQ ID NO: 1 are those having the substitution in one of more of the following positions: N21D, D97N, V128I K177L, M200L, L204YF, E242QA, G477K and G478K and/or deletion in position R179 and/or S180 or of I181 and/or G182. Most preferred amylase variants of SEQ ID NO: 1 are those having the substitutions:

N21D+D97N+V128I wherein the variants optionally further comprise a substitution at position 200 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO2011/098531, WO2013/001078 and WO2013/001087.

Commercially available amylases are Duramyl™, Termamyl™, Fungamyl™, Stainzyme™, Stainzyme Plus™, Natalase™, Liquozyme X and BAN™ (from Novozymes A/S), and Rapidase™, Purastar™/Effectenz™, Powerase, Preferenz S1000, Preferenz S100 and Preferenz S110 (from Genencor International Inc./DuPont).

Proteases:

Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those derived from Bacillus such as Bacillus lentus, B. alkalophilus, B. subtilis, B. amyloliquefaciens, Bacillus pumilus and Bacillus gibsonii described in; U.S. Pat. No. 7,262,042 and WO09/021867, and subtilisin lentus, subtilisin Novo, subtilisin Carlsberg, Bacillus licheniformis, subtilisin BPN', subtilisin 309, subtilisin 147 and subtilisin 168 described in WO89/06279 and protease PD138 described in (WO93/18140). Other useful proteases may be those described in WO 92/175177, WO 01/016285, WO 02/026024 and WO 02/016547. Examples of trypsin-like proteases are trypsin (e.g. of porcine or bovine origin) and the Fusarium protease described in WO 89/06270, WO 94/25583 and WO 05/040372, and the chymotrypsin proteases derived from Cellumonas described in WO 05/052161 and WO 05/052146.

A further preferred protease is the alkaline protease from Bacillus lentus DSM 5483, as described for example in WO 95/23221, and variants thereof which are described in WO 92/21760, WO 95/23221, EP 1921147 and EP 1921148.

Examples of metalloproteases are the neutral metalloprotease as described in WO07/044993 (Genencor Int.) such as those derived from Bacillus amyloliquefaciens.

Examples of useful proteases are the variants described in: WO 92/19729, WO 96/034946, WO 98/20115, WO 98/20116, WO 99/011768, WO 01/44452, WO 03/006602, WO 04/03186, WO 04/041979, WO 07/006305, WO 11/036263, WO 11/036264, especially the variants with substitutions in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269 wherein the positions correspond to the positions of the Bacillus lentus protease shown in SEQ ID NO 1 of WO 2016/001449. More preferred the subtilase variants may comprise one or more of the mutations: S3T, V4I, S9R, S9E, A15T, S24G, S24R, K27R, N42R, S55P, G59E, G59D, N60D, N60E, V66A, N74D, N85S, N85R, G96S, G96A, S97G, S97D, S97A, S97SD, S99E, S99D, S99G, S99M, S99N, S99R, S99H, S101A, V102I, V102Y, V102N, S104A, G116V, G116R, H118D, H118N, N120S, S126L, P127Q, S128A, S154D, A156E, G157D, G157P, S158E, Y161A, R164S, Q176E, N179E, S182E, Q185N, A188P, G189E, V193M, N198D, V199I, Y203W, S206G, L211Q, L211D, N212D, N212S, M216S, A226V, K229L, Q230H, Q239R, N246K, N255W, N255D, N255E, L256E, L256D T268A or R269H. The protease variants are preferably variants of the Bacillus lentus protease (Savinase®) shown in SEQ ID NO 1 of WO 2016/001449, the Bacillus amyloliquefaciens protease (BPN') shown in SEQ ID NO 2 of WO2016/001449. The protease variants preferably have at least 80% sequence identity to SEQ ID NO 1 or SEQ ID NO 2 of WO 2016/001449.

A protease variant comprising a substitution at one or more positions corresponding to positions 171, 173, 175, 179, or 180 of SEQ ID NO: 1 of WO2004/067737, wherein said protease variant has a sequence identity of at least 75% but less than 100% to SEQ ID NO: 1 of WO 2004/067737.

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Blaze®, Blaze Evity® 100T, Blaze Evity® 125T, Blaze Evity® 150T, Neutrase®, Everlase® and Esperase® (Novozymes A/S), those sold under the tradename Maxatase®, Maxacal®, Maxapem®, Purafect Ox®, Purafect OxP®, Puramax®, FN2®, FN3®, FN4®, Excellase®, Excellenz P1000™, Excellenz P1250™, Eraser®, Preferenz P100™, Purafect Prime®, Preferenz P110™, Effectenz P1000™, Purafect®™, Effectenz P1050™, Purafect Ox®™, Effectenz P2000™, Purafast®, Properase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (Bacillus alkalophilus subtilisin) from Kao.

Peroxidases/Oxidases

A peroxidase according to the invention is a peroxidase enzyme comprised by the enzyme classification EC 1.11.1.7, as set out by the Nomenclature Committee of the International Union of Biochemistry and Molecular Biology (IUBMB), or any fragment derived therefrom, exhibiting peroxidase activity.

Suitable peroxidases include those of plant, bacterial or fungal origin. Chemically modified or protein engineered mutants are included. Examples of useful peroxidases include peroxidases from Coprinopsis, e.g., from C. cinerea (EP 179,486), and variants thereof as those described in WO 93/24618, WO 95/10602, and WO 98/15257.

A suitable peroxidase includes a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions. Preferably, the haloperoxidase is a vanadium haloperoxidase, i.e., a vanadate-containing haloperoxidase. Haloperoxidases have been isolated from many different fungi, in particular from the fungus group dematiaceous hyphomycetes, such as Caldariomyces, e.g., C. fumago, Alternaria, Curvularia, e.g., C. verruculosa and C. inaequalis, Drechslera, Ulocladium and Botrytis.

Haloperoxidases have also been isolated from bacteria such as Pseudomonas, e.g., P. pyrrocinia and Streptomyces, e.g., S. aureofaciens.

A suitable oxidase includes in particular, any laccase enzyme comprised by the enzyme classification EC 1.10.3.2, or any fragment derived therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5). Preferred laccase enzymes are enzymes of microbial origin. The enzymes may be derived from plants, bacteria or fungi (including filamentous fungi and yeasts). Suitable examples from fungi include a laccase derivable from a strain of *Aspergillus, Neurospora*, e.g., *N. crassa, Podospora, Botrytis, Collybia, Fomes, Lentinus, Pleurotus, Trametes*, e.g., *T. villosa* and *T. versicolor, Rhizoctonia*, e.g., *R. solani, Coprinopsis*, e.g., *C. cinerea, C. comatus, C. friesii*, and *C. plicatilis, Psathyrella*, e.g., *P. condelleana, Panaeolus*, e.g., *P. papilionaceus, Myceliophthora*, e.g., *M. thermophila, Schytalidium*, e.g., *S. thermophilum, Polyporus*, e.g., *P. pinsitus, Phlebia*, e.g., *P. radiata* (WO 92/01046), or *Coriolus*, e.g., *C. hirsutus* (JP 2238885). Suitable examples from bacteria include a laccase derivable from a strain of *Bacillus*. A laccase derived from *Coprinopsis* or *Myceliophthora* is preferred; in particular, a laccase derived from *Coprinopsis cinema*, as disclosed in WO 97/08325; or from *Myceliophthora thermophila*, as disclosed in WO 95/33836.

Dispersants

The detergent compositions of the present invention can also contain dispersants. In particular, powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents

The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent

The detergent compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2.2'-disulfonate, 4,4'-bis-(2-anilino-4-(N-methyl-N-2-hydroxy-ethylamino)-s-triazin-6-ylamino) stilbene-2,2'-disulfonate, 4,4'-bis-(4-phenyl-1,2,3-triazol-2-yl)stilbene-2,2'-disulfonate and sodium 5-(2H-naphtho[1,2-d][1,2,3] triazol-2-yl)-2-[(E)-2-phenylvinyl]benzenesulfonate.
Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins. Suitable fluorescent brightener levels include lower levels of from about 0.01, from 0.05, from about 0.1 or even from about 0.2 wt % to upper levels of 0.5 or even 0.75 wt %.

Soil Release Polymers

The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers is amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore, random graft co-polymers are suitable soil release polymers. Suitable graft co-polymers are described in more detail in WO 2007/138054, WO 2006/108856 and WO 2006/113314 (hereby incorporated by reference). Suitable polyethylene glycol polymers include random graft co-polymers comprising: (i) hydrophilic backbone comprising polyethylene glycol; and (ii) side chain(s) selected from the group consisting of: C4-C25 alkyl group, polypropylene, polybutylene, vinyl ester of a saturated C1-C6 mono-carboxylic acid, C1-C6 alkyl ester of acrylic or methacrylic acid, and mixtures thereof. Suitable polyethylene glycol polymers have a polyethylene glycol backbone with random grafted polyvinyl acetate side chains. The average molecular weight of the polyethylene glycol backbone can be in the range of from 2,000 Da to 20,000 Da, or from 4,000 Da to 8,000 Da. The molecular weight ratio of the polyethylene glycol backbone to the polyvinyl acetate side chains can be in the range of from 1:1 to 1:5, or from 1:1.2 to 1:2. The average number of graft sites per ethylene oxide units can be less than 1, or less than 0.8, the average number of graft sites per ethylene oxide units can be in the range of from 0.5 to 0.9, or the average number of graft sites per ethylene oxide units can be in the range of from 0.1 to 0.5, or from 0.2 to 0.4. A suitable polyethylene glycol polymer is Sokalan HP22. Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents

The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Rheology Modifiers

The detergent compositions of the present invention may also include one or more rheology modifiers, structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040. Other suitable cleaning composition components include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Formulation of Detergent Products

The detergent composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid.

Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blended compositions comprising hydrolytically degradable and water soluble polymer blends such as polylactide and polyvinyl alcohol (known under the Trade reference M8630 as sold by MonoSol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids: US2009/0011970 A1.

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent. A liquid or gel detergent may be non-aqueous.

Granular Detergent Formulations

The composition(s) of the invention may be formulated as a granule for example as a co-granule that combines one or more enzymes. Each enzyme will then be present in more granules securing a more uniform distribution of enzymes in the detergent. This also reduces the physical segregation of different enzymes due to different particle sizes. Methods for producing multi-enzyme co-granulates for the detergent industry are disclosed in the IP.com disclosure IPCOM000200739D.

Another example of formulation of enzymes by the use of co-granulates are disclosed in WO 2013/188331, which relates to a detergent composition comprising (a) a multi-enzyme co-granule; (b) less than 10 wt zeolite (anhydrous basis); and (c) less than 10 wt phosphate salt (anhydrous basis), wherein said enzyme co-granule comprises from 10 to 98 wt % moisture sink component and the composition additionally comprises from 20 to 80 wt % detergent moisture sink component. A multi-enzyme co-granule may comprise an DNase of the invention and (a) one or more enzymes selected from lipases, cellulases, xyloglucanases, perhydrolases, peroxidases, lipoxygenases, laccases, hemicellulases, proteases, care cellulases, cellobiose dehydrogenases, xylanases, phospho lipases, esterases, cutinases, pectinases, mannanases, pectate lyases, keratinases, reductases, oxidases, phenoloxidases, ligninases, pullulanases, tannases, pentosanases, lichenases glucanases, arabinosidases, hyaluronidase, chondroitinase, amylases, and mixtures thereof.

In one aspect, the present invention provides a granule, which comprises:
  (a) a core comprising a polypeptide comprising the amino acid sequence shown in SEQ ID NO 3, SEQ ID NO 6, SEQ ID NO 9 or polypeptides having at least 80% sequence identity hereto, and
  (b) optionally a coating consisting of one or more layer(s) surrounding the core.

Uses

The polypeptides of the invention having DNase activity may be used for deep cleaning of an item, such as a textile. One embodiment of the invention relates to the use of a DNase according to the invention for prevention reduction or removal of malodor. One embodiment of the invention relates to the use of an DNase of the invention for prevention or reduction of anti-redeposition and improvement of whiteness of a textile subjected to multiple washes. One embodiment of the invention relates to the use of a polypeptide according to the invention for deep cleaning of an item, wherein the item is a textile. One embodiment of the invention relates to the use of a polypeptide according to the invention
  (i) for preventing, reducing or removing stickiness of the item;
  (ii) for pretreating stains on the item;
  (iii) for preventing, reducing or removing redeposition of soil during a wash cycle;
  (iv) for preventing, reducing or removing adherence of soil to the item;

(v) for maintaining or improving whiteness of the item;
(vi) for preventing, reducing or removal malodor from the item,
wherein the item is a textile.

The invention is further summarized in the following paragraphs:

1. Use of a polypeptide having DNase activity and comprising one or more of the motif(s) C[DN]TRE (SEQ ID NO 15), [DN]SAEK (SEQ ID NO 16) for deep cleaning of an item, wherein the item is a textile.
2. Use according to paragraph 1 for preventing, reducing or removing stickiness of the item.
3. Use according to any of paragraphs 1 or 2 for pre-treating stains on the item.
4. Use according to any of paragraphs 1-3 for preventing, reducing or removing re-deposition of soil during a wash cycle.
5. Use according to any of paragraphs 1-4 for preventing, reducing or removing adherence of soil to the item.
6. Use according to any of the preceding paragraphs for maintaining or improving the whiteness of the item.
7. Use according to any of the preceding paragraphs, wherein a malodor is reduced or removed from the item.
8. Use according to any of the preceding composition paragraphs, wherein the surface is a textile surface.
9. Use according to any of the preceding composition paragraphs, wherein the textile is made of cotton, cotton/polyester, polyester, polyamide, polyacrylic and/or silk.
10. Use according to any of the preceding paragraphs, wherein the polypeptide is a polypeptide of paragraphs 39-47
11. A composition comprising a polypeptide having DNase activity, the polypeptide comprising one or more of the motif(s) C[DN]TRE (SEQ ID NO 15) or [DN]SAEK (SEQ ID NO 16), and at least one detergent adjunct ingredient.
12. Composition according to paragraph 11, wherein the polypeptide is the polypeptide of paragraphs 39-47.
13. Composition according to any of the preceding composition paragraphs, wherein the detergent adjunct ingredient is selected from the group consisting of surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric huing agents, anti-foaming agents, dispersants, processing aids, and/or pigments.
14. Composition according to any of the preceding composition paragraphs wherein the composition comprises from about 5 wt % to about 50 wt %, from about 5 wt % to about 40 wt %, from about 5 wt % to about 30 wt %, from about 5 wt % to about 20 wt %, from about 5 wt % to about 10 wt % anionic surfactant, preferably selected from linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.
15. Composition according to any of the preceding composition paragraphs wherein the composition comprises from about 10 wt % to about 50 wt % of at least one builder, preferably selected from citric acid, methylglycine-N,N-diacetic acid (MGDA) and/or glutamic acid-N,N-diacetic acid (GLDA) and mixtures thereof.
16. Composition according to any of the preceding paragraphs comprising from about 5 wt % to about 40 wt % nonionic surfactant, and from about 0 wt % to about 5 wt % anionic surfactant.
17. Composition according to paragraph 16, wherein the nonionic surfactant is selected from alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA) and combinations thereof.
18. Composition according to any of the preceding composition paragraphs, wherein the composition further comprises one or more enzymes selected from the group consisting of proteases, lipases, cutinases, amylases, carbohydrases, cellulases, pectinases, mannanases, arabinases, galactanases, xylanases and oxidases.
19. Composition according to any of the preceding composition paragraphs, wherein the composition is a bar, a homogenous tablet, a tablet having two or more layers, a pouch having one or more compartments, a regular or compact powder, a granule, a paste, a gel, or a regular, compact or concentrated liquid.
20. Composition according to any of the preceding composition paragraphs, wherein the composition is a cleaning composition selected from liquid detergent, powder detergent and granule detergent compositions.
21. Composition according to any of the preceding composition paragraphs wherein the polypeptide comprises one or more motif(s) C[DN]TRE (SEQ ID NO 15), [DN]SAEK (SEQ ID NO 16) and wherein the polypeptide is selected from the group consisting of polypeptides having the amino acid sequence of SEQ ID NO 3, SEQ ID NO 6, SEQ ID 9 and polypeptides having at least 80% sequence identity hereto.
22. Composition according to any of the preceding composition paragraphs wherein the polypeptide comprising one or more motif(s) C[DN]TRE (SEQ ID NO 15) or [DN]SAEK (SEQ ID NO 16) comprises the amino acid sequence shown in SEQ ID NO 3 or a sequence having at least 60% sequence identity hereto, e.g. at least 70%, at least 80% or at least 90%.
23. Composition according to any of the preceding composition paragraphs wherein the polypeptide comprising one or more motif(s) C[DN]TRE (SEQ ID NO 15) or [DN]SAEK (SEQ ID NO 16) comprises the amino acid sequence shown in SEQ ID NO 6 or a sequence having at least 60% sequence identity hereto, e.g. at least 70%, at least 80% or at least 90%.

24. Composition according to any of the preceding composition paragraphs wherein the polypeptide comprising one or more motif(s) C[DN]TRE (SEQ ID NO 15) or [DN]SAEK (SEQ ID NO 16) comprises the amino acid sequence shown in SEQ ID NO 9 or a sequence having at least 60% sequence identity hereto, e.g. at least 70%, at least 80% or at least 90%.

25. A method for laundering an item comprising the steps of:
   a. Exposing an item to a wash liquor comprising a polypeptide of paragraphs 39-47 or a composition according to any of paragraphs 11-24;
   b. Completing at least one wash cycle; and
   c. Optionally rinsing the item,
   wherein the item is a textile.

26. A method of treating an item, wherein the item is preferably a textile, said method comprising the step of exposing an item to a polypeptide selected from the group consisting of a polypeptide having at least 80% sequence identity to the mature polypeptide shown in SEQ ID NO: 3, SEQ ID NO: 6, SEQ ID NO: 9, a wash liquor comprising said polypeptide or a detergent composition according to any preceding paragraph.

27. Method according to any preceding paragraph, wherein the pH of the wash liquor is in the range of 1 to 11.

28. Method according to any of the preceding method paragraphs, wherein the pH of the wash liquor is in the range 5.5 to 11, such as in the range of 7 to 9, in the range of 7 to 8 or in the range of 7 to 8.5.

29. Method according to any of the preceding method paragraphs, wherein the temperature of the wash liquor is in the range of 5° C. to 95° C., or in the range of 10° C. to 80° C., in the range of 10° C. to 70° C., in the range of 10° C. to 60° C., in the range of 10° C. to 50° C., in the range of 15° C. to 40° C., in the range of 20° C. to 40° C., in the range of 15° C. to 30° C. or in the range of 20° C. to 30° C.

30. Method according to any of the preceding method paragraphs, wherein the temperature of the wash liquor is from about 20° C. to about 40° C.

31. Method according to any of the preceding method paragraphs, wherein the temperature of the wash liquor is from about 15° C. to about 30° C.

32. Method according to any of the preceding method paragraphs, wherein stains present on the item is pretreated with a polypeptide of paragraphs 39-47 or a detergent composition according to any of paragraphs 11-24.

33. Method according to any of the preceding method paragraphs, wherein stickiness of the item is reduced.

34. Method according to any of the preceding method paragraphs, wherein redeposition of soil is reduced.

35. Method according to any of the preceding method paragraphs, wherein adherence of soil to the item is reduced or removed.

36. Method according to any of the preceding method paragraphs, wherein whiteness of the item is maintained or improved.

37. Method according to any of the preceding method paragraphs, wherein malodor is reduced or removed from the item.

38. Method according to any of the preceding method paragraphs, wherein the concentration of the polypeptide having DNase activity in the wash liquor is at least 0,001 mg of polypeptide, such as at least 5 mg of protein, preferably at least 10 mg of protein, more preferably at least 15 mg of protein, per liter of wash liquor, optionally the concentration of polypeptide in the wash liquor is in the range 0,002 mg/L to 2 mg/L, such as 0.02 mg/L til 2 mg/L, such as 0.2 mg/L to 2 mg/L or in the range of 0,0001 mg/L to 10 mg/L or in the range of in the range of 0,001 mg/L to 10 mg/L, or in the range of 0.01 mg/L to 10 mg/L, or in the range of 0.1 mg/L to 10 mg/L per liter of wash liquor, optionally the concentration of the polypeptide of the invention is 0.0001% to 2 wt %, such as 0.001 to 0.1 wt %, such as 0.005 to 0.1 wt %, such as 0.01 to 0.1 wt %, such as 0.01 to 0.5 wt % or most preferred 0.002 to 0.09 wt % in the total detergent concentration.

39. A polypeptide having DNase activity, selected from the group consisting of:
   a. a polypeptide having at least 80% sequence identity to the mature polypeptide of SEQ ID NO: 2, SEQ ID NO: 5, SEQ ID NO: 8 or a polypeptide having at least 80% sequence identity to the mature polypeptide shown in SEQ ID NO: 3, SEQ ID NO: 6 or SEQ ID NO: 9;
   b. a polypeptide encoded by a polynucleotide that hybridizes under low stringency conditions with
      i. the mature polypeptide coding sequence of SEQ ID NO: 1, SEQ ID NO: 4, SEQ ID NO: 7;
      ii. the cDNA sequence thereof, or
      iii. the full-length complement of (i) or (ii);
   c. a polypeptide encoded by a polynucleotide having at least 60% sequence identity to the mature polypeptide coding sequence of SEQ ID NO: 1, SEQ ID NO: 4, SEQ ID NO: 7 or the cDNA sequence thereof;
   d. a variant of the mature polypeptide shown in SEQ ID NO: 3, SEQ ID NO: 6, SEQ ID NO: 9 comprising a substitution, deletion, and/or insertion at one or more positions or a variant of the mature polypeptide shown in SEQ ID NO: 3, SEQ ID NO: 6, SEQ ID NO: 9 comprising a substitution, deletion, and/or insertion at one or more positions; and
   e. a fragment of the polypeptide of (a), (b), (c), or (d) that comprises one or more motif(s) C[DN]TRE (SEQ ID NO 15) or [DN]SAEK (SEQ ID NO 16).

40. The polypeptide of paragraph 39, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2, SEQ ID NO: 5, SEQ ID NO: 8 or to the mature polypeptide shown in SEQ ID NO: 3, SEQ ID NO: 6, SEQ ID NO: 9.

41. The polypeptide of paragraph 39 or 40, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2 or to the mature polypeptide shown in SEQ ID NO: 3.

42. The polypeptide of paragraph 39 or 40, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 5 or to the mature polypeptide shown in SEQ ID NO: 6.

43. The polypeptide of paragraph 39 or 40, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 8 or to the mature polypeptide shown in SEQ ID NO: 9.

44. The polypeptide according to any of paragraphs 39 to 43, which is encoded by a polynucleotide that hybridizes under low stringency conditions, low-medium stringency conditions, medium stringency conditions, medium-high stringency conditions, high stringency conditions, or very high stringency conditions with
   i. the mature polypeptide coding sequence of SEQ ID NO: 1, SEQ ID NO: 4, SEQ ID NO: 7;
   ii. the cDNA sequence thereof, or
   iii. the full-length complement of (i) or (ii).

45. The polypeptide according to any of paragraphs 41 to 44, which is encoded by a polynucleotide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 1, SEQ ID NO: 4, SEQ ID NO: 7 or the cDNA sequence thereof.

46. The polypeptide according to any of paragraphs 41 to 44, comprising or consisting of SEQ ID NO: 3, SEQ ID NO: 6, SEQ ID NO: 9 or the mature polypeptide of SEQ ID NO: 2, SEQ ID NO: 5, SEQ ID NO: 8.

47. The polypeptide according to any of paragraphs 41 to 44, which is a variant of the any of the polypeptides with SEQ ID NO: 3, SEQ ID NO: 6, SEQ ID NO: 9, comprising a substitution, deletion, and/or insertion at one or more positions.

48. A polynucleotide encoding the polypeptide according to any of paragraphs 41-47.

49. A nucleic acid construct or expression vector comprising the polynucleotide of paragraph 76 operably linked to one or more optionally heterologous control sequences that direct the production of the polypeptide in an expression host.

50. A recombinant host cell comprising the polynucleotide of paragraph 48 operably linked to one or more optionally heterologous control sequences that direct the production of the polypeptide.

51. A method of producing the polypeptide of any of paragraphs 39-47, comprising cultivating a cell, which in its wild-type form produces the polypeptide, under conditions conducive for production of the polypeptide.

52. The method of paragraph 51, further comprising recovering the polypeptide.

53. A method of producing a polypeptide according to any of paragraphs 39-47, comprising cultivating the host cell of paragraph 50 under conditions conducive for production of the polypeptide.

54. The method of paragraph 53, further comprising recovering the polypeptide.

55. A nucleic acid construct or expression vector comprising a gene encoding a protein operably linked to the polynucleotide of paragraph 48, wherein the gene is foreign or heterologous to the polynucleotide encoding the signal peptide.

56. A recombinant host cell comprising a gene encoding a protein operably linked to the polynucleotide of paragraph 48, wherein the gene is foreign or heterologous to the polynucleotide encoding the signal peptide.

57. A method of producing a protein, comprising cultivating a recombinant host cell comprising a gene encoding a protein operably linked to the polynucleotide of paragraph 48, wherein the gene is foreign to the polynucleotide encoding the signal peptide, under conditions conducive for production of the protein.

58. The method of paragraph 57, further comprising recovering the protein.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

EXAMPLES

Assay I
Testing of DNase Activity

DNase activity may be determined on DNase Test Agar with Methyl Green (BD, Franklin Lakes, N.J., USA), which is prepared according to the manual from the supplier. Briefly, 21 g of agar is dissolved in 500 ml water and then autoclaved for 15 min at 121° C. Autoclaved agar is tempered to 48° C. in a water bath, and 20 ml of agar is poured into Petri dishes and allowed to solidify by incubation overnight at room temperature. On solidified agar plates, 5 µl of enzyme solutions are added, and DNase activity is observed as colorless zones around the spotted enzyme solutions.

Assay II

DNase activity may be determined by fluorescence using a fluorescence-quenched DNA oligonucleotide probe. This probe emits a signal after nuclease degradation according to the manual from the supplier (DNase alert kit, Integrated DNA Technology, Coralville, Iowa, USA). Briefly, 5 µl of the substrate is added to 95 µl of DNase. If the signal is too high, further dilutions of DNase are performed in a suitable buffer. Kinetic curves are measured for 20 min at 22° C. using a Clariostar microplate reader (536 nm excitation, 556 nm emission).

Example 1: Cloning and Expression of Bacterial DNases

The DNases were derived from bacterial strains isolated from environmental samples by standard microbiological isolation techniques. Isolated pure strains were identified and taxonomy was assigned based on DNA sequencing of the 16S ribosomal genes (Table 1). The strains *Saccharothrix australiensis* (DSM43800) and *Kutzneria albida* (DSM43870) were purchased from Deutsche Sammlung von Mikroorganismen und Zellkulturen (DSMZ, Braunschweig, Germany)

TABLE 1

| Strain | Source Country | Mature protein SEQ ID: |
| --- | --- | --- |
| *Streptomyces* sp-63712 | United States | 3 |
| *Saccharothrix australiensis* | Australia | 6 |
| *Kutzneria albida* | Japan | 9 |

Chromosomal DNA was isolated from pure cultures of the individual strains with the DNeasy Blood & Tissue Kit from Qiagen (Hilden, Germany) and subjected to full genome sequencing using Illumina technology. Genome sequencing, the subsequent assembly of reads and the gene discovery (i.e. annotation of gene functions) are known to the person skilled in the art and the services can be purchased commercially. The genome sequences were analyzed for putative DNases from the PFAM database family PF07510 (R. D. Finn et al. Nucleic Acids Research (2014), 42:D222-D230) this analysis identified three genes encoding putative DNases, which were subsequently cloned and recombinantly expressed in Bacillus subtilis. The genes encoding the DNase were amplified by PCR and fused with regulatory elements, affinity purification tag and homology regions for recombination into the pectate lysase locus of the B. subtilis genome. The linear integration construct was a SOE-PCR fusion product (Horton, R. M., Hunt, H. D., Ho, S. N., Pullen, J. K. and Pease, L. R. (1989) Engineering hybrid genes without the use of restriction enzymes, gene splicing by overlap extension Gene 77: 61-68) made by fusion of the gene between two Bacillus subtilis chromosomal regions along with strong promoters and a chloramphenicol resistance marker. The SOE PCR method is also described in patent application WO2003/095658. The genes were expressed under the control of a triple promoter system (as described in WO 99/43835), consisting of the promoters from Bacillus licheniformis alpha-amylase gene (amyL), Bacillus amyloliquefaciens alpha-amylase gene (amyQ), and the Bacillus thuringiensis cryIIIA promoter including stabilizing sequence. The genes were fused with DNA encoding a Bacillus clausii secretion signal (encoding the following amino acid sequence: MKKPLGKIVASTAL-LISVAFSSSIASA (SEQ ID NO 18)) replacing the native secretion signal. Furthermore, the expression construct results in the addition of a carboxy-terminal poly histidine tail consisting of the amino acid sequence HHHHHH (SEQ ID NO 10) to the mature DNases.

The SOE-PCR products were transformed into Bacillus subtilis and integrated in the chromosome by homologous recombination into the pectate lyase locus. Subsequently a recombinant Bacillus subtilis clone containing the integrated expression construct was grown in liquid culture. The culture broth was centrifuged (20000×g, 20 min) and the supernatant was carefully decanted from the precipitate and used for purification of the enzyme or alternatively sterile filtered supernatant was used directly for assays.

Example 2: Purification of Recombinant Enzymes by Nickel Affinity Chromatography The pH of the cleared supernatant was adjusted to pH 8, filtrated through a 0.2 µM filter, and the supernatant applied to a 5 ml HisTrap™ excel column. Prior to loading, the column had been equilibrated in 5 column volumes (CV) of 50 mM Tris/HCl pH 8. In order to remove unbound material, the column was washed with 8 CV of 50 mM Tris/HCl pH 8, and elution of the target was obtained with 50 mM HEPES pH 7+10 mM imidazole. The eluted protein was desalted on a HiPrep™ 26/10 desalting column, equilibrated using 3 CV of 50 mM HEPES pH 7+100 mM NaCl. This buffer was also used for elution of the target, and the flow rate was 10 ml/min. Relevant fractions were selected and pooled based on the chromatogram and SDS-PAGE analysis.

Example 3: Wash Data

Preparation of Biofilm Swatches

Biofilm swatches were made by growing Brevundimonas sp. on polyester swatches for two days. The biofilm swatches were rinsed twice in water and dried for 1 h under a flow and subsequently punched into small circles and stored at 4° C. for further use.

Wash Experiment

Biofilm swatch punctures were placed in a deep well 96 format plate. The 96 well plate was placed in a Hamilton robot and subjected to a wash simulation program using the following conditions: Shaking speed: 30 sec at 1000 rpm. Duration of wash cycle: 30 minutes with shaking; temperature 30° C.; Volume of wash liquor (total): 0.5 ml per well. (490 wash liquor+10 uL sample).

Model detergent A wash liquor (100%) was prepared by dissolving 3.33 g/l of model detergent A containing 12% LAS, 11% AEO Biosoft N25-7 (NI), 5% AEOS (SLES), 6% MPG (mono propylene glycol), 3% ethanol, 3% TEA (triethanolamine), 2.75% cocoa soap, 2.75% soya soap, 2% glycerol, 2% sodium hydroxide, 2% sodium citrate, 1% sodium formiate, 0.2% DTMPA and 0.2% PCA (Propenoic acid=acrylic maleic copolymer)(all percentages are w/w (weight volume) in water with hardness 15 dH.

For wash performance of Streptomyces sp. 63712 DNase (SEQ ID NO 3), Kutzneria albida (SEQ ID NO 9) and Saccharothrix australiensis DNase (SEQ ID NO 6), Model detergent A (3.3 g/L) were dissolved in water and water hardness adjusted to 15° dH. Soil was subsequently added to reach a concentration of 0.7 g soil/L (WFK 09V pigment soil). A 96 well plate was filled with each enzyme sample, and the program was started on the robot. The Streptomyces sp. 63712 DNase (SEQ ID NO 3), Kutzneria albida (SEQ ID NO 9) and Saccharothrix australiensis DNase (SEQ ID NO 6) were tested each in the concentration of 0.05 ppm. The blank consisted of biofilm swatches without any enzyme addition. After completion of the wash simulation cycle, the swatch punctures were removed from the wash liquor and dried on a filter paper. The dried swatch punctures were fixed on a sheet of white paper for scanning. The scanned picture was further used with the software colour-analyzer. Each sample has an intensity measurement from the colour analyzer software analysis that is used to calculate the delta intensity (remission), by subtracting the intensity of the blank, without enzyme. Values over 70 are visual for the human eye.

TABLE 2

Wash performance of Streptomyces sp. 63712 DNase (SEQ ID NO 3) and Saccharothrix australiensis DNase (SEQ ID NO 6) in model detergent A.

| | REM Without enzyme | REM With enzyme | ΔREM |
|---|---|---|---|
| Streptomyces sp. 63712 (SEQ ID NO 3) | 257.6 | 352.4 | 94.8 |
| Saccharothrix australiensis (SEQ ID NO 6) | 257.6 | 348.9 | 91.3 |
| Kutzneria albida (SEQ ID NO 9) | 331 | 258 | 74 |

Example 4: Construction of Phylogenetic Trees

The NUC1 domain includes the polypeptides of the invention having DNase activity and comprises the NUC1_A domain as well as the clusters such as the clades.

A phylogenetic tree was constructed of polypeptide sequences containing a DUF1524 domain as defined in PFAM (PF07510, Pfam version 30.0 Finn (2016). Nucleic Acids Research, Database Issue 44:D279-D285). The phylogenetic tree was constructed from a multiple alignment of mature polypeptide sequences containing at least one DUF1524 domain. The sequences were aligned using the MUSCLE algorithm version 3.8.31 (Edgar, 2004. *Nucleic Acids Research* 32(5): 1792-1797), and the phylogenetic trees were constructed using FastTree version 2.1.8 (Price et al., 2010, *PloS one* 5(3)) and visualized using iTOL (Letunic & Bork, 2007. *Bioinformatics* 23(1): 127-128).

The polypeptides comprising the DUF1524 PFAM domain also comprise several short peptide motifs. One example is [E/D/H]H[I/V/L/F/M]X[P/A/S] (SEQ ID NO 11) situated in positions corresponding to positions 89 to 93 in K. *albida* (SEQ ID NO 9). H90 is a catalytic residue involved in the catalytic activity of DUF1524, and part of the HXXP motif.

The polypeptides comprising the DUF1524 PFAM domain can be separated into distinct sub-clusters. The sub-clusters are defined by one or more short sequence motifs, as well as by containing a DUF1524 domain as defined in PFAM (PF07510, Pfam version 30.0). We denoted one sub-cluster comprising the motif [F/L/Y/I]A[N/R]D[L/I/P/V] (SEQ ID NO 12) as family NUC1. Another motif characteristic of the NUC1 domain is C[DIN]T[A/R] (SEQ ID NO 13). All polypeptide sequences containing a DUF1524 as well as the two motifs will be denoted as containing a NUC1 domain.

Generation of NUC1_A Domain

A phylogenetic tree was constructed of polypeptide sequences containing a NUC1 domain, as defined above. The phylogenetic tree was constructed from a multiple alignment of mature polypeptide sequences containing at least one NUC1 domain. The sequences were aligned using the MUSCLE algorithm version 3.8.31 (Edgar, 2004. *Nucleic Acids Research* 32(5): 1792-1797), and the tree was constructed using FastTree version 2.1.8 (Price et al., 2010, *PloS one* 5(3)) and visualized using iTOL (Letunic & Bork, 2007. *Bioinformatics* 23(1): 127-128). The polypeptides in NUC1 can be separated into at least two distinct sub-clusters, where one was denoted NUC1_A. A characteristic motif for this sub-cluster is the motif [DQ][IV]D[H] (SEQ ID NO 3) corresponding to amino acid 87 to 90 in the reference polypeptide (SEQ ID NO 9). The D at the position corresponding to position 89 of SEQ ID NO 9 is predicted to be involved in binding of catalytic metal ion cofactor.

Generation of Phylogenetic Trees

A phylogenetic tree was constructed of polypeptide sequences containing a DUF1524 domain, a NUC1 domain, and a NUC1_A domain, as defined above. The phylogenetic tree was constructed from a multiple alignment of mature polypeptide sequences containing at least one NUC1_A domain. The sequences were aligned using the MUSCLE algorithm version 3.8.31 (Edgar, 2004. *Nucleic Acids Research* 32(5): 1792-1797), and the tree was constructed using FastTree version 2.1.8 (Price et al., 2010, *PloS one* 5(3)) and visualized using iTOL (Letunic & Bork, 2007, *Bioinformatics* 23(1): 127-128). The polypeptides in NUC1_A can be separated into multiple distinct sub-clusters, or clades, where we denoted the clades listed below. The distinct motifs for each clade are described in details below.

Generation of CNTRE Clade

The CNTRE clade comprises polypeptides of fungal origin containing a DUF1524 domain, a NUC1 domain and a NUC1_A domain, and having DNase activity. The polypeptides of the clade comprise the motifs C[DN]TRE (SEQ ID NO: 15), corresponding to positions 44 to 48 of SEQ ID NO 9 and [DN]SAEK (SEQ ID NO: 16), corresponding to positions 168 to 172 of SEQ ID NO 9.

An alignment of the polypeptides of the invention comprised in the clade is shown in FIG. 1.

The invention claimed is:

1. A composition comprising:
    (a) at least one detergent adjunct ingredient; and
    (b) a polypeptide having DNase activity, selected from the group consisting of:
        (i) a polypeptide having at least 95% sequence identity to the polypeptide of SEQ ID NO: 3;
        (ii) a polypeptide having at least 90% sequence identity to the polypeptide of SEQ ID NO: 6;
        (iii) a polypeptide comprising the polypeptide of (i) or (ii) and an N-terminal and/or C-terminal His-tag and/or HQ-tag;
        (iv) a polypeptide comprising the polypeptide of (i) or (ii) and an N-terminal and/or C-terminal extension of between 1 and 10 amino acids; and
        (v) a fragment of the polypeptide of (i) or (ii) having DNase activity and having at least 90% of the length of SEQ ID NO: 3 or SEQ ID NO: 6;
    wherein the composition is in the form of a bar, a homogenous tablet, a tablet having two or more layers, a pouch having one or more compartments, a regular or compact powder, a granule, a paste, a gel, or a regular, compact or concentrated liquid.

2. The composition of claim 1, wherein the polypeptide has at least 95% sequence identity to the polypeptide of SEQ ID NO: 3.

3. The composition of claim 1, wherein the polypeptide has at least 97% sequence identity to the polypeptide of SEQ ID NO: 3.

4. The composition of claim 1, wherein the polypeptide has at least 90% sequence identity to the polypeptide of SEQ ID NO: 6.

5. The composition of claim 1, wherein the polypeptide has at least 95% sequence identity to the polypeptide of SEQ ID NO: 6.

6. The composition of claim 1, wherein the polypeptide has at least 97% sequence identity to the polypeptide of SEQ ID NO: 6.

7. The composition of claim 1, wherein the polypeptide is
    (a) a variant of the polypeptide of SEQ ID NO: 3 and has at least 95% sequence identity to the polypeptide of SEQ ID NO: 3; or
    (b) a variant of the polypeptide of SEQ ID NO: 6 and has at least 90% sequence identity to the polypeptide of SEQ ID NO: 6.

8. The composition of claim 1, wherein the polypeptide comprises the amino acid sequence of SEQ ID NO: 3.

9. The composition of claim 1, wherein the polypeptide comprises the amino acid sequence of SEQ ID NO: 6.

10. The composition of claim 1, wherein the polypeptide is a fragment of the polypeptide shown in SEQ ID NO: 3, wherein the fragment has DNase activity and at least 90% of the length of SEQ ID NO: 3.

11. The composition of claim 1, wherein the polypeptide is a fragment of the polypeptide shown in SEQ ID NO: 6, wherein the fragment has DNase activity and at least 90% of the length of SEQ ID NO: 6.

12. The composition of claim 1, wherein the composition is a cleaning or detergent composition, an automatic dish wash composition or a laundry composition.

13. A method for laundering a textile, comprising:
    a. exposing the textile to a wash liquor comprising the composition of claim 1; and
    b. completing at least one wash cycle.

14. The method of claim 13, further comprising rinsing the textile.

15. A recombinant host cell comprising multiple copies of a polynucleotide encoding a polypeptide having DNase activity, which is operably linked to one or more control sequences that direct the production of the polypeptide, wherein the polypeptide is selected from the group consisting of:
    (a) a polypeptide having at least 95% sequence identity to the polypeptide of SEQ ID NO: 3;
    (b) a polypeptide having at least 90% sequence identity to the polypeptide of SEQ ID NO: 6;
    (c) a polypeptide comprising the polypeptide of (a) or (b) and an N-terminal and/or C-terminal His-tag and/or HQ-tag;
    (d) a polypeptide comprising the polypeptide of (a) or (b) and an N-terminal and/or C-terminal extension of between 1 and 10 amino acids; and
    (e) a fragment of the polypeptide of (a) or (b) having DNase activity and having at least 90% of the length of SEQ ID NO: 3 or SEQ ID NO: 6.

16. A method of producing a polypeptide having DNase activity, comprising cultivating the host cell of claim 15 under conditions conducive for production of the polypeptide.

17. The method of claim 16, wherein the polypeptide has at least 95% sequence identity to the polypeptide of SEQ ID NO: 3 or 6.

18. The method of claim 16, wherein the host cell is selected from the group consisting of *Bacillus, Campylobacter, Clostridium, Enterococcus, E. coli, Flavobacterium, Fusobacterium, Geobacillus, Helicobacter, Ilyobacter, Lactobacillus, Lactococcus, Neisseria, Oceanobacillus, Pseudomonas, Salmonella, Staphylococcus, Streptococcus, Streptomyces*, and *Ureaplasma* cells.

19. The method of claim 16, wherein the host cell is selected from the group consisting of *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, and *Trichoderma* cells.

\* \* \* \* \*

SEQUENCE LISTING

```
<160> NUMBER OF SEQ ID NOS: 18

<210> SEQ ID NO 1
<211> LENGTH: 645
<212> TYPE: DNA
<213> ORGANISM: Streptomyces sp-63712
<220> FEATURE:
<221> NAME/KEY: CDS
<222> LOCATION: (1)..(642)
<220> FEATURE:
<221> NAME/KEY: sig_peptide
<222> LOCATION: (1)..(96)
<220> FEATURE:
<221> NAME/KEY: mat_peptide
<222> LOCATION: (97)..(642)

<400> SEQUENCE: 1 atg gca aag gtc tac gcg cgt cga gtt tcc atc gcc gcg ggt tcg gcc      48
Met Ala Lys Val Tyr Ala Arg Arg Val Ser Ile Ala Ala Gly Ser Ala
    -30                 -25                 -20 gcg gcc ctg gtc tgc acg ctg atg ctg agc ggc cag acc gcc cag gca      96
Ala Ala Leu Val Cys Thr Leu Met Leu Ser Gly Gln Thr Ala Gln Ala
    -15                 -10                 -5                  -1 gcg ccg ccc agc ccg ccc agc gcg gcc acc gca cgg acg tac ctc acc     144
Ala Pro Pro Ser Pro Pro Ser Ala Ala Thr Ala Arg Thr Tyr Leu Thr
1               5                   10                  15 gag atc aag gag cag ccc gag ggc ccg cag gac ggc tac agc cgc gac     192
```

```
Glu Ile Lys Glu Gln Pro Glu Gly Pro Gln Asp Gly Tyr Ser Arg Asp
            20                  25                  30 aag ttc ccg cac tgg atc gac cag ggg aac aac tgc aac acc cgc gag      240
Lys Phe Pro His Trp Ile Asp Gln Gly Asn Asn Cys Asn Thr Arg Glu
            35                  40                  45 gtg gtg ctc aag cgt gat ggc acc aac gtg cag cag gac ggc agc tgt      288
Val Val Leu Lys Arg Asp Gly Thr Asn Val Gln Gln Asp Gly Ser Cys
 50                  55                  60 gcg gcg gtc ggc ggc acc tgg gtc tcc gcg tac gac ggc gcg acc tgg      336
Ala Ala Val Gly Gly Thr Trp Val Ser Ala Tyr Asp Gly Ala Thr Trp
 65                  70                  75                  80 acc cag gcg tcc gac ctc gac atc gac cat gtc gta ccg ctg tcg gag      384
Thr Gln Ala Ser Asp Leu Asp Ile Asp His Val Val Pro Leu Ser Glu
                    85                  90                  95 gcg tgg aag tcg ggc gcc gcg cag tgg acc acc gcg aag cgt cag gag      432
Ala Trp Lys Ser Gly Ala Ala Gln Trp Thr Thr Ala Lys Arg Gln Glu
                100                 105                 110 ctc gcc aac gac ctg acg cac tcc cag ctg atc gcc gtc acc gac aac      480
Leu Ala Asn Asp Leu Thr His Ser Gln Leu Ile Ala Val Thr Asp Asn
                115                 120                 125 gtc aac cag gcc aag ggc gac aag gac ccg gcg aac tgg ctg ccg ccg      528
Val Asn Gln Ala Lys Gly Asp Lys Asp Pro Ala Asn Trp Leu Pro Pro
    130                 135                 140 aag gcg tcg tac cac tgc gag tac gcc cgg atg tgg gtg tgg gtg aag      576
Lys Ala Ser Tyr His Cys Glu Tyr Ala Arg Met Trp Val Trp Val Lys
145                 150                 155                 160 cat gag tac ggc atg acc gcg gac tcc gcg gag aag gcc gcc ctg aag      624
His Glu Tyr Gly Met Thr Ala Asp Ser Ala Glu Lys Ala Ala Leu Lys
                165                 170                 175 aag atc ctg gac ggc tgc tga                                          645
Lys Ile Leu Asp Gly Cys
                180

<210> SEQ ID NO 2
<211> LENGTH: 214
<212> TYPE: PRT
<213> ORGANISM: Streptomyces sp-63712

<400> SEQUENCE: 2

Met Ala Lys Val Tyr Ala Arg Arg Val Ser Ile Ala Ala Gly Ser Ala
        -30                 -25                 -20

Ala Ala Leu Val Cys Thr Leu Met Leu Ser Gly Gln Thr Ala Gln Ala
        -15                 -10                  -5                  -1

Ala Pro Pro Ser Pro Ser Ala Ala Thr Ala Arg Thr Tyr Leu Thr
  1               5                  10                  15

Glu Ile Lys Glu Gln Pro Glu Gly Pro Gln Asp Gly Tyr Ser Arg Asp
            20                  25                  30

Lys Phe Pro His Trp Ile Asp Gln Gly Asn Asn Cys Asn Thr Arg Glu
            35                  40                  45

Val Val Leu Lys Arg Asp Gly Thr Asn Val Gln Gln Asp Gly Ser Cys
 50                  55                  60

Ala Ala Val Gly Gly Thr Trp Val Ser Ala Tyr Asp Gly Ala Thr Trp
 65                  70                  75                  80

Thr Gln Ala Ser Asp Leu Asp Ile Asp His Val Val Pro Leu Ser Glu
                    85                  90                  95

Ala Trp Lys Ser Gly Ala Ala Gln Trp Thr Thr Ala Lys Arg Gln Glu
                100                 105                 110

Leu Ala Asn Asp Leu Thr His Ser Gln Leu Ile Ala Val Thr Asp Asn
```

```
              115                 120                 125
Val Asn Gln Ala Lys Gly Asp Lys Asp Pro Ala Asn Trp Leu Pro Pro
130                 135                 140

Lys Ala Ser Tyr His Cys Glu Tyr Ala Arg Met Trp Val Trp Val Lys
145                 150                 155                 160

His Glu Tyr Gly Met Thr Ala Asp Ser Ala Glu Lys Ala Ala Leu Lys
                165                 170                 175

Lys Ile Leu Asp Gly Cys
            180

<210> SEQ ID NO 3
<211> LENGTH: 182
<212> TYPE: PRT
<213> ORGANISM: Streptomyces sp-63712

<400> SEQUENCE: 3

Ala Pro Pro Ser Pro Ser Ala Ala Thr Ala Arg Thr Tyr Leu Thr
1               5                   10                  15

Glu Ile Lys Glu Gln Pro Glu Gly Pro Gln Asp Gly Tyr Ser Arg Asp
                20                  25                  30

Lys Phe Pro His Trp Ile Asp Gln Gly Asn Asn Cys Asn Thr Arg Glu
            35                  40                  45

Val Val Leu Lys Arg Asp Gly Thr Asn Val Gln Gln Asp Gly Ser Cys
50                  55                  60

Ala Ala Val Gly Gly Thr Trp Val Ser Ala Tyr Asp Gly Ala Thr Trp
65                  70                  75                  80

Thr Gln Ala Ser Asp Leu Asp Ile Asp His Val Val Pro Leu Ser Glu
                85                  90                  95

Ala Trp Lys Ser Gly Ala Ala Gln Trp Thr Thr Ala Lys Arg Gln Glu
            100                 105                 110

Leu Ala Asn Asp Leu Thr His Ser Gln Leu Ile Ala Val Thr Asp Asn
        115                 120                 125

Val Asn Gln Ala Lys Gly Asp Lys Asp Pro Ala Asn Trp Leu Pro Pro
130                 135                 140

Lys Ala Ser Tyr His Cys Glu Tyr Ala Arg Met Trp Val Trp Val Lys
145                 150                 155                 160

His Glu Tyr Gly Met Thr Ala Asp Ser Ala Glu Lys Ala Ala Leu Lys
                165                 170                 175

Lys Ile Leu Asp Gly Cys
            180

<210> SEQ ID NO 4
<211> LENGTH: 630
<212> TYPE: DNA
<213> ORGANISM: Saccharothrix australiensis
<220> FEATURE:
<221> NAME/KEY: CDS
<222> LOCATION: (1)..(627)
<220> FEATURE:
<221> NAME/KEY: sig_peptide
<222> LOCATION: (1)..(81)
<220> FEATURE:
<221> NAME/KEY: mat_peptide
<222> LOCATION: (82)..(627)

<400> SEQUENCE: 4 ttg tta cgg atc agc aca gcc ccg ctc acc ctg ttc ctg acc ggc gcg    48
Leu Leu Arg Ile Ser Thr Ala Pro Leu Thr Leu Phe Leu Thr Gly Ala
        -25                 -20                 -15
```

-continued

| | |
|---|---|
| ctc gtc ctc ggc gtc gcc gcg ccc gcg gcg gcc acg ccg ccc gac atc<br>Leu Val Leu Gly Val Ala Ala Pro Ala Ala Ala Thr Pro Pro Asp Ile<br>    -10                    -5                    -1  1               5 | 96 |
| ccc ggc acg gcc acc gcc cag gcc gag ctg gcc ggg ctc acc gtc gcc<br>Pro Gly Thr Ala Thr Ala Gln Ala Glu Leu Ala Gly Leu Thr Val Ala<br>                10                          15                      20 | 144 |
| gcc gag ggc tcg acg gcg ggc tac tcg cgc gac ctg ttc ccg cac tgg<br>Ala Glu Gly Ser Thr Ala Gly Tyr Ser Arg Asp Leu Phe Pro His Trp<br>            25                      30                      35 | 192 |
| acc acc gtc tcc ggc acg tgc aac acg cgg gag acg gtg ctc aag cgc<br>Thr Thr Val Ser Gly Thr Cys Asn Thr Arg Glu Thr Val Leu Lys Arg<br>      40                      45                      50 | 240 |
| gac ggc acg tcc gtg gtc acc gac gcc tcc tgc gcc gcg acg tcc ggc<br>Asp Gly Thr Ser Val Val Thr Asp Ala Ser Cys Ala Ala Thr Ser Gly<br>55                    60                      65 | 288 |
| cgc tgg tac agc ccg tac gac ggg gcc acc tgg agc gcg gcg tcc gac<br>Arg Trp Tyr Ser Pro Tyr Asp Gly Ala Thr Trp Ser Ala Ala Ser Asp<br>70                    75                      80                  85 | 336 |
| gtg gac atc gac cac gtc gtg ccg ctg gcc gag gcg tgg cgg tcc ggc<br>Val Asp Ile Asp His Val Val Pro Leu Ala Glu Ala Trp Arg Ser Gly<br>                90                      95                      100 | 384 |
| gcg tcc tcg tgg acc acc gcg cgg cgg cag tcg ttc gcc aac gac ctc<br>Ala Ser Ser Trp Thr Thr Ala Arg Arg Gln Ser Phe Ala Asn Asp Leu<br>            105                     110                    115 | 432 |
| gcc gga ccg cag ctg atc gcc gtg acg gac gac gtg aac cag gcc aag<br>Ala Gly Pro Gln Leu Ile Ala Val Thr Asp Asp Val Asn Gln Ala Lys<br>        120                     125                    130 | 480 |
| ggc gac cag gac ccg gcg cgg tgg cag ccg ccg ctg acc tcc tac cgg<br>Gly Asp Gln Asp Pro Ala Arg Trp Gln Pro Pro Leu Thr Ser Tyr Arg<br>135                    140                      145 | 528 |
| tgc acc tac gcc aag atg tgg gtg cac acc aag cac cgg tgg ggc ctg<br>Cys Thr Tyr Ala Lys Met Trp Val His Thr Lys His Arg Trp Gly Leu<br>150                    155                      160                  165 | 576 |
| aag gtc gac tcc gcc gag aag tcc gcg ttg cag tcg atg ctc ggg agg<br>Lys Val Asp Ser Ala Glu Lys Ser Ala Leu Gln Ser Met Leu Gly Arg<br>              170                     175                    180 | 624 |
| tgc tga<br>Cys | 630 |

<210> SEQ ID NO 5
<211> LENGTH: 209
<212> TYPE: PRT
<213> ORGANISM: Saccharothrix australiensis

<400> SEQUENCE: 5

Leu Leu Arg Ile Ser Thr Ala Pro Leu Thr Leu Phe Leu Thr Gly Ala
        -25                    -20                        -15

Leu Val Leu Gly Val Ala Ala Pro Ala Ala Ala Thr Pro Pro Asp Ile
    -10                    -5                    -1  1              5

Pro Gly Thr Ala Thr Ala Gln Ala Glu Leu Ala Gly Leu Thr Val Ala
                10                          15                      20

Ala Glu Gly Ser Thr Ala Gly Tyr Ser Arg Asp Leu Phe Pro His Trp
            25                      30                      35

Thr Thr Val Ser Gly Thr Cys Asn Thr Arg Glu Thr Val Leu Lys Arg
      40                      45                      50

Asp Gly Thr Ser Val Val Thr Asp Ala Ser Cys Ala Ala Thr Ser Gly
55                    60                      65

Arg Trp Tyr Ser Pro Tyr Asp Gly Ala Thr Trp Ser Ala Ala Ser Asp
70                    75                      80                  85

Val Asp Ile Asp His Val Val Pro Leu Ala Glu Ala Trp Arg Ser Gly
            90                  95                 100

Ala Ser Ser Trp Thr Thr Ala Arg Arg Gln Ser Phe Ala Asn Asp Leu
        105                 110                 115

Ala Gly Pro Gln Leu Ile Ala Val Thr Asp Asp Val Asn Gln Ala Lys
            120                 125                 130

Gly Asp Gln Asp Pro Ala Arg Trp Gln Pro Pro Leu Thr Ser Tyr Arg
135                 140                 145

Cys Thr Tyr Ala Lys Met Trp Val His Thr Lys His Arg Trp Gly Leu
150                 155                 160                 165

Lys Val Asp Ser Ala Glu Lys Ser Ala Leu Gln Ser Met Leu Gly Arg
            170                 175                 180

Cys

<210> SEQ ID NO 6
<211> LENGTH: 182
<212> TYPE: PRT
<213> ORGANISM: Saccharothrix australiensis

<400> SEQUENCE: 6

Thr Pro Pro Asp Ile Pro Gly Thr Ala Thr Ala Gln Ala Glu Leu Ala
1               5                   10                  15

Gly Leu Thr Val Ala Ala Glu Gly Ser Thr Ala Gly Tyr Ser Arg Asp
            20                  25                  30

Leu Phe Pro His Trp Thr Thr Val Ser Gly Thr Cys Asn Thr Arg Glu
        35                  40                  45

Thr Val Leu Lys Arg Asp Gly Thr Ser Val Val Thr Asp Ala Ser Cys
    50                  55                  60

Ala Ala Thr Ser Gly Arg Trp Tyr Ser Pro Tyr Asp Gly Ala Thr Trp
65                  70                  75                  80

Ser Ala Ala Ser Asp Val Asp Ile Asp His Val Val Pro Leu Ala Glu
                85                  90                  95

Ala Trp Arg Ser Gly Ala Ser Ser Trp Thr Thr Ala Arg Arg Gln Ser
            100                 105                 110

Phe Ala Asn Asp Leu Ala Gly Pro Gln Leu Ile Ala Val Thr Asp Asp
        115                 120                 125

Val Asn Gln Ala Lys Gly Asp Gln Asp Pro Ala Arg Trp Gln Pro Pro
    130                 135                 140

Leu Thr Ser Tyr Arg Cys Thr Tyr Ala Lys Met Trp Val His Thr Lys
145                 150                 155                 160

His Arg Trp Gly Leu Lys Val Asp Ser Ala Glu Lys Ser Ala Leu Gln
                165                 170                 175

Ser Met Leu Gly Arg Cys
            180

<210> SEQ ID NO 7
<211> LENGTH: 873
<212> TYPE: DNA
<213> ORGANISM: Kutzneria albida
<220> FEATURE:
<221> NAME/KEY: CDS
<222> LOCATION: (1)..(636)
<220> FEATURE:
<221> NAME/KEY: sig_peptide
<222> LOCATION: (1)..(90)
<220> FEATURE:
<221> NAME/KEY: mat_peptide
<222> LOCATION: (91)..(636)

<400> SEQUENCE: 7

```
atg aat agt ttt cgt gcc gta cgc ggg ctg tta gcc gcc gga gcg ctg      48
Met Asn Ser Phe Arg Ala Val Arg Gly Leu Leu Ala Ala Gly Ala Leu
-30             -25                 -20                 -15 tcg gtg gtc gcg gtc ctc ggg gtg agc acc ccg gcc tcc gcg acc ccg      96
Ser Val Val Ala Val Leu Gly Val Ser Thr Pro Ala Ser Ala Thr Pro
            -10                 -5                  -1   1 ccg aac atc ccg gac aag acc acc gcg gtg aac gag ctc aac ggg ctg     144
Pro Asn Ile Pro Asp Lys Thr Thr Ala Val Asn Glu Leu Asn Gly Leu
         5                  10                  15 cgg gtc cag ccc gac ggc tcc tcc gcc ggc tac tcg cgg gac aag ttc     192
Arg Val Gln Pro Asp Gly Ser Ser Ala Gly Tyr Ser Arg Asp Lys Phe
     20                  25                  30 aag cac tgg atc acc atc gag ggc agc tgc aac acc cgc gag atg gtg     240
Lys His Trp Ile Thr Ile Glu Gly Ser Cys Asn Thr Arg Glu Met Val
 35                  40                  45                  50 ctc aag cgc gac ggc acg aac gtg cag acc gac tcc tcc tgc gcg gcc     288
Leu Lys Arg Asp Gly Thr Asn Val Gln Thr Asp Ser Ser Cys Ala Ala
                 55                  60                  65 aag tcc ggc acc tgg tac agc ccg tac gac ggc tcc acg caa acc agc     336
Lys Ser Gly Thr Trp Tyr Ser Pro Tyr Asp Gly Ser Thr Gln Thr Ser
             70                  75                  80 gcc tcg gcc atc cag atc gac cac atg gtg ccg ctg gcc gac gcc tgg     384
Ala Ser Ala Ile Gln Ile Asp His Met Val Pro Leu Ala Asp Ala Trp
         85                  90                  95 cgc acc ggc gcc tcc ggc tgg acc gcg cag cgg cgc cag gac ttc gcc     432
Arg Thr Gly Ala Ser Gly Trp Thr Ala Gln Arg Arg Gln Asp Phe Ala
100                 105                 110 aac gac ctg agc tac ccg cag ctg gtg gcc gtc aag ggc gcg gtg aac     480
Asn Asp Leu Ser Tyr Pro Gln Leu Val Ala Val Lys Gly Ala Val Asn
115                 120                 125                 130 gag tcc aag ggc gac aag tca ccc gat ctg tgg aag cct ccg ctg acc     528
Glu Ser Lys Gly Asp Lys Ser Pro Asp Leu Trp Lys Pro Pro Leu Thr
                135                 140                 145 tcg tac tgg tgc acg tac gcg aag atg tgg acg cac gtg aag tcc aag     576
Ser Tyr Trp Cys Thr Tyr Ala Lys Met Trp Thr His Val Lys Ser Lys
            150                 155                 160 tac tcg ctc act gtc aac tcc gcg gag aag agc gct ctg cag gac atg     624
Tyr Ser Leu Thr Val Asn Ser Ala Glu Lys Ser Ala Leu Gln Asp Met
        165                 170                 175 ctc ggt agg tgc tgatggccga atactcgtcc ccgttcgcgt ctggccccgg         676
Leu Gly Arg Cys
        180 cggggtgatg accgacgacg tcggggtgat caccggcgac ctcgaactgc gcaccgaggc   736 cggcgaggac ggactcgtct cggtgtacgt gcgctacgag gaggcggacg agtggtaccg   796 gctgcgcggg gcctcgtgcg tggtgcacga cccgcgcgac caccgggcgc tgcacatggc   856 gctgctcggt gtgctga                                                  873
```

<210> SEQ ID NO 8
<211> LENGTH: 212
<212> TYPE: PRT
<213> ORGANISM: Kutzneria albida

<400> SEQUENCE: 8

```
Met Asn Ser Phe Arg Ala Val Arg Gly Leu Leu Ala Ala Gly Ala Leu
-30             -25                 -20                 -15

Ser Val Val Ala Val Leu Gly Val Ser Thr Pro Ala Ser Ala Thr Pro
```

```
                -10              -5              -1  1
Pro Asn Ile Pro Asp Lys Thr Thr Ala Val Asn Glu Leu Asn Gly Leu
            5               10              15

Arg Val Gln Pro Asp Gly Ser Ser Ala Gly Tyr Ser Arg Asp Lys Phe
        20              25              30

Lys His Trp Ile Thr Ile Glu Gly Ser Cys Asn Thr Arg Glu Met Val
35              40              45              50

Leu Lys Arg Asp Gly Thr Asn Val Gln Thr Asp Ser Ser Cys Ala Ala
                55              60              65

Lys Ser Gly Thr Trp Tyr Ser Pro Tyr Asp Gly Ser Thr Gln Thr Ser
            70              75              80

Ala Ser Ala Ile Gln Ile Asp His Met Val Pro Leu Ala Asp Ala Trp
        85              90              95

Arg Thr Gly Ala Ser Gly Trp Thr Ala Gln Arg Arg Gln Asp Phe Ala
    100             105             110

Asn Asp Leu Ser Tyr Pro Gln Leu Val Ala Val Lys Gly Ala Val Asn
115             120             125             130

Glu Ser Lys Gly Asp Lys Ser Pro Asp Leu Trp Lys Pro Pro Leu Thr
            135             140             145

Ser Tyr Trp Cys Thr Tyr Ala Lys Met Trp Thr His Val Lys Ser Lys
            150             155             160

Tyr Ser Leu Thr Val Asn Ser Ala Glu Lys Ser Ala Leu Gln Asp Met
            165             170             175

Leu Gly Arg Cys
    180
```

<210> SEQ ID NO 9
<211> LENGTH: 182
<212> TYPE: PRT
<213> ORGANISM: Kutzneria albida

<400> SEQUENCE: 9

```
Thr Pro Pro Asn Ile Pro Asp Lys Thr Thr Ala Val Asn Glu Leu Asn
1               5               10              15

Gly Leu Arg Val Gln Pro Asp Gly Ser Ser Ala Gly Tyr Ser Arg Asp
            20              25              30

Lys Phe Lys His Trp Ile Thr Ile Glu Gly Ser Cys Asn Thr Arg Glu
        35              40              45

Met Val Leu Lys Arg Asp Gly Thr Asn Val Gln Thr Asp Ser Ser Cys
    50              55              60

Ala Ala Lys Ser Gly Thr Trp Tyr Ser Pro Tyr Asp Gly Ser Thr Gln
65              70              75              80

Thr Ser Ala Ser Ala Ile Gln Ile Asp His Met Val Pro Leu Ala Asp
            85              90              95

Ala Trp Arg Thr Gly Ala Ser Gly Trp Thr Ala Gln Arg Arg Gln Asp
        100             105             110

Phe Ala Asn Asp Leu Ser Tyr Pro Gln Leu Val Ala Val Lys Gly Ala
    115             120             125

Val Asn Glu Ser Lys Gly Asp Lys Ser Pro Asp Leu Trp Lys Pro Pro
130             135             140

Leu Thr Ser Tyr Trp Cys Thr Tyr Ala Lys Met Trp Thr His Val Lys
145             150             155             160

Ser Lys Tyr Ser Leu Thr Val Asn Ser Ala Glu Lys Ser Ala Leu Gln
            165             170             175
```

Asp Met Leu Gly Arg Cys
        180

<210> SEQ ID NO 10
<211> LENGTH: 6
<212> TYPE: PRT
<213> ORGANISM: Artificial
<220> FEATURE:
<223> OTHER INFORMATION: Histidine tail

<400> SEQUENCE: 10

His His His His His His
1               5

<210> SEQ ID NO 11
<211> LENGTH: 5
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: X = E (Glu), D (Asp), H (His)
<220> FEATURE:
<221> NAME/KEY: MISC_FEATURE
<222> LOCATION: (3)..(3)
<223> OTHER INFORMATION: X = I (Ile), V (Val), L (Leu), F (Phe), M (Met)
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: X = P (Pro), A (Ala), S (Ser)

<400> SEQUENCE: 11

Xaa His Xaa Xaa Xaa
1               5

<210> SEQ ID NO 12
<211> LENGTH: 5
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: X= F (Phe), L (Leu), Y (Tyr), I (Ile)
<220> FEATURE:
<221> NAME/KEY: MISC_FEATURE
<222> LOCATION: (3)..(3)
<223> OTHER INFORMATION: X= N (Asn), R (Arg)
<220> FEATURE:
<221> NAME/KEY: MISC_FEATURE
<222> LOCATION: (5)..(5)
<223> OTHER INFORMATION: X= L (Leu), I (Ile), P (Pro), V (Val)

<400> SEQUENCE: 12

Xaa Ala Xaa Asp Xaa
1               5

<210> SEQ ID NO 13
<211> LENGTH: 4
<212> TYPE: PRT
<213> ORGANISM: Artificial
<220> FEATURE:
<223> OTHER INFORMATION: Motif
<220> FEATURE:
<221> NAME/KEY: MISC_FEATURE

```
<222> LOCATION: (2)..(2)
<223> OTHER INFORMATION: X= D (Asp),  N (Asn)
<220> FEATURE:
<221> NAME/KEY: MISC_FEATURE
<222> LOCATION: (4)..(4)
<223> OTHER INFORMATION: X= A (Ala), R (Arg)

<400> SEQUENCE: 13

Cys Xaa Thr Xaa
1

<210> SEQ ID NO 14
<211> LENGTH: 4
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: X=D (Asp), Q (Gln)
<220> FEATURE:
<221> NAME/KEY: MISC_FEATURE
<222> LOCATION: (2)..(2)
<223> OTHER INFORMATION: X=I (Ile), V (Val)

<400> SEQUENCE: 14

Xaa Xaa Asp His
1

<210> SEQ ID NO 15
<211> LENGTH: 5
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (2)..(2)
<223> OTHER INFORMATION: X = D (Asp), N (Asn)

<400> SEQUENCE: 15

Cys Xaa Thr Arg Glu
1               5

<210> SEQ ID NO 16
<211> LENGTH: 5
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: X= D (Asp), N (Asn)

<400> SEQUENCE: 16

Xaa Ser Ala Glu Lys
1               5

<210> SEQ ID NO 17
<211> LENGTH: 5
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: X= D (Asp), N (Asn)
<220> FEATURE:
```

```
<221> NAME/KEY: MISC_FEATURE
<222> LOCATION: (3)..(3)
<223> OTHER INFORMATION: X= T (Thr), D (Asp), S (Ser), P (Pro)

<400> SEQUENCE: 17

Xaa Ala Xaa Gly Tyr
1               5

<210> SEQ ID NO 18
<211> LENGTH: 27
<212> TYPE: PRT
<213> ORGANISM: bacillus clausii

<400> SEQUENCE: 18

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala
            20                  25
```